(12) United States Patent
Aravamudan et al.

(10) Patent No.: US 12,211,598 B1
(45) Date of Patent: Jan. 28, 2025

(54) CONFIGURING A GENERATIVE MACHINE LEARNING MODEL USING A SYNTACTIC INTERFACE

(71) Applicant: nference, Inc., Cambridge, MA (US)

(72) Inventors: Murali Aravamudan, Andover, MA (US); Ajit Rajasekharan, West Windsor, NJ (US)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 18/750,203

(22) Filed: Jun. 21, 2024

(51) Int. Cl.
*G16H 10/60* (2018.01)
*G06F 16/2455* (2019.01)

(52) U.S. Cl.
CPC ......... *G16H 10/60* (2018.01); *G06F 16/2455* (2019.01)

(58) Field of Classification Search
CPC ........ G06Q 10/10; G16H 50/30; G16H 50/70; G16H 15/00; G16H 40/63; G16H 40/20; G16H 50/20; G16H 40/67; G16H 10/60; G06F 16/2455
See application file for complete search history.

(56) References Cited

U.S. PATENT DOCUMENTS

| | | | | |
|---|---|---|---|---|
| 8,660,859 B1* | 2/2014 | Ansari | ................... | G16H 10/60 705/2 |
| 9,690,861 B2* | 6/2017 | Boloor | ................... | G16H 10/60 |
| 9,750,408 B1* | 9/2017 | Martin | ................. | A61B 5/0205 |
| 10,368,846 B2* | 8/2019 | Venkataramani | ......... | G06T 7/11 |
| 10,552,931 B2* | 2/2020 | Sheffer | .................. | G16H 70/20 |
| 11,031,109 B2* | 6/2021 | Devarakonda | ........ | G06F 3/0482 |
| 11,210,606 B1* | 12/2021 | Morgan | ................. | G16H 40/20 |
| 11,250,950 B1* | 2/2022 | Miller | ................... | G06F 18/214 |
| 11,315,685 B2* | 4/2022 | Malhotra | ............. | A61B 5/4848 |
| 11,393,466 B2* | 7/2022 | Kim | ....................... | G16H 10/60 |
| 11,748,566 B1* | 9/2023 | Lam | ..................... | G06F 40/284 704/9 |
| 2013/0066870 A1* | 3/2013 | Somasundaran | ....... | G06F 16/35 707/E17.091 |
| 2014/0055098 A1* | 2/2014 | Lee | ........................ | H02J 50/10 320/137 |

(Continued)

FOREIGN PATENT DOCUMENTS

CN 116975927 A 10/2023

*Primary Examiner* — Ninos Donabed
(74) *Attorney, Agent, or Firm* — Caldwell Intellectual Property Law

(57) ABSTRACT

Described herein are a system, method, and device for configuring a generative machine learning model using a syntactic interface. A system may include a user interface, a memory, and a processor configured to, using a syntactic interface displayed using the user interface, receive a syntactic interface input from a user; identify an electronic medical record (EMR) by generating an EMR database query as a function of the syntactic interface input, querying an EMR database using the EMR database query, and receiving, from the EMR database, an EMR database response; generate a prompt as a function of the syntactic interface input; generate a first generative model output as a function of the prompt and the EMR using a trained generative machine learning model; and using a conversational interface displayed using the user interface, display the first generative model output to the user.

16 Claims, 9 Drawing Sheets

(56) References Cited

U.S. PATENT DOCUMENTS

| | | | | |
|---|---|---|---|---|
| 2015/0370979 | A1* | 12/2015 | Boloor | G16H 15/00 |
| | | | | 705/3 |
| 2016/0019299 | A1* | 1/2016 | Boloor | G06F 16/9535 |
| | | | | 705/3 |
| 2016/0132686 | A1* | 5/2016 | Peng | G06F 21/604 |
| | | | | 726/28 |
| 2016/0210427 | A1* | 7/2016 | Mynhier | G16H 10/60 |
| 2016/0239611 | A1* | 8/2016 | Heldt | G16H 70/60 |
| 2017/0161435 | A1* | 6/2017 | Orosco | G16H 10/60 |
| 2017/0322684 | A1* | 11/2017 | Hermosillo Valadez | |
| | | | | G16H 10/20 |
| 2018/0000462 | A1* | 1/2018 | Venkataramani | G06T 7/11 |
| 2018/0018590 | A1* | 1/2018 | Szeto | G16H 50/20 |
| 2019/0206517 | A1* | 7/2019 | Devarakonda | G16H 50/70 |
| 2020/0126550 | A1* | 4/2020 | Kim | G16H 10/60 |
| 2020/0185102 | A1* | 6/2020 | Leventhal | G06F 40/117 |
| 2020/0312457 | A1 | 10/2020 | Kasthurirathne et al. | |
| 2020/0410601 | A1* | 12/2020 | Laumeyer | G06F 40/186 |
| 2021/0280286 | A1* | 9/2021 | Ravindranathan | |
| | | | | A61N 1/36021 |
| 2021/0322100 | A1* | 10/2021 | Roche | A61B 90/37 |
| 2021/0326421 | A1* | 10/2021 | Khoury | G10L 17/08 |
| 2022/0102004 | A1* | 3/2022 | Abend | G16H 50/20 |
| 2022/0178712 | A1* | 6/2022 | Marinescu | G01C 21/3461 |
| 2022/0183880 | A1* | 6/2022 | Wong | A61N 1/303 |
| 2022/0230714 | A1* | 7/2022 | Batman | G16H 40/67 |
| 2023/0158187 | A1* | 5/2023 | Bonansinga | A61L 2/10 |
| | | | | 422/24 |
| 2023/0316104 | A1* | 10/2023 | Ott | G06N 3/048 |
| | | | | 706/46 |
| 2023/0334263 | A1* | 10/2023 | Konam | G16H 10/20 |
| 2024/0047044 | A1* | 2/2024 | Wisser | G16H 10/60 |

\* cited by examiner

CONFIGURING A GENERATIVE MACHINE LEARNING MODEL USING A SYNTACTIC INTERFACE

FIELD OF THE INVENTION

The present invention generally relates to the field of machine learning. In particular, the present invention is directed to configuring a generative machine learning model using a syntactic interface.

BACKGROUND

Inputs into large language models are typically determined using an interface which allows free-form inputs. Platforms including generative machine learning models often allow users to generate an output based only on a freeform input, such as a text input. Traditional processes for collecting inputs for generative models may require a user to input the same information multiple times in order to get a desired result.

SUMMARY OF THE DISCLOSURE

In an aspect, a system for configuring a generative machine learning model using a syntactic interface may include a user interface; at least a processor; and a memory communicatively connected to the at least processor, wherein the memory contains instructions configuring the at least processor to, using a syntactic interface displayed using the user interface, receive a syntactic interface input from a user; identify an electronic medical record (EMR) by generating an EMR database query as a function of the syntactic interface input, querying an EMR database using the EMR database query, and receiving, from the EMR database, an EMR database response; generate a prompt as a function of the syntactic interface input; generate a first generative model output as a function of the prompt and the EMR using a trained generative machine learning model; and using a conversational interface displayed using the user interface, display the first generative model output to the user.

In another aspect, a method of configuring a generative machine learning model using a syntactic interface may include, using at least a processor and a syntactic interface displayed using a user interface, receiving a syntactic interface input from a user; using the at least a processor, identifying an electronic medical record (EMR) by generating an EMR database query as a function of the syntactic interface input, querying an EMR database using the EMR database query, and receiving, from the EMR database, an EMR database response; using the at least a processor, generating a prompt as a function of the syntactic interface input; using the at least a processor, generating a first generative model output as a function of the prompt and the EMR using a trained generative machine learning model; and using the at least a processor and a conversational interface displayed using the user interface, displaying the first generative model output to the user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for configuring a generative machine learning model using a syntactic interface. In some embodiments, a computing device may receive a syntactic interface input, such as a selection of an interface element or movement of a slider. Such syntactic interface input may be used to generate a prompt and an electronic medical record (EMR) database query. Such EMR database query may be used to query an EMR database, and response of such database, as well as a prompt generated based on syntactic interface input, may be used to generate a generative model output. Such generative model output may be displayed to a user using a conversational interface. In some embodiments, a computing device may receive an input using a conversational interface, such as a follow up question or a request to edit information presented in a particular way. Such use of a syntactic interface and a conversational interface may allow a machine learning model used to, in a non-limiting example, receive inputs more efficiently, as data from user interactions with other aspects of an interface may be used to generate inputs suitable for a machine learning model. In another non-limiting example, use of these systems and methods may allow user specific settings for machine learning models to be more efficiently preserved across uses of a model. Exemplary implementations of these concepts are described further herein.

Figure 1:
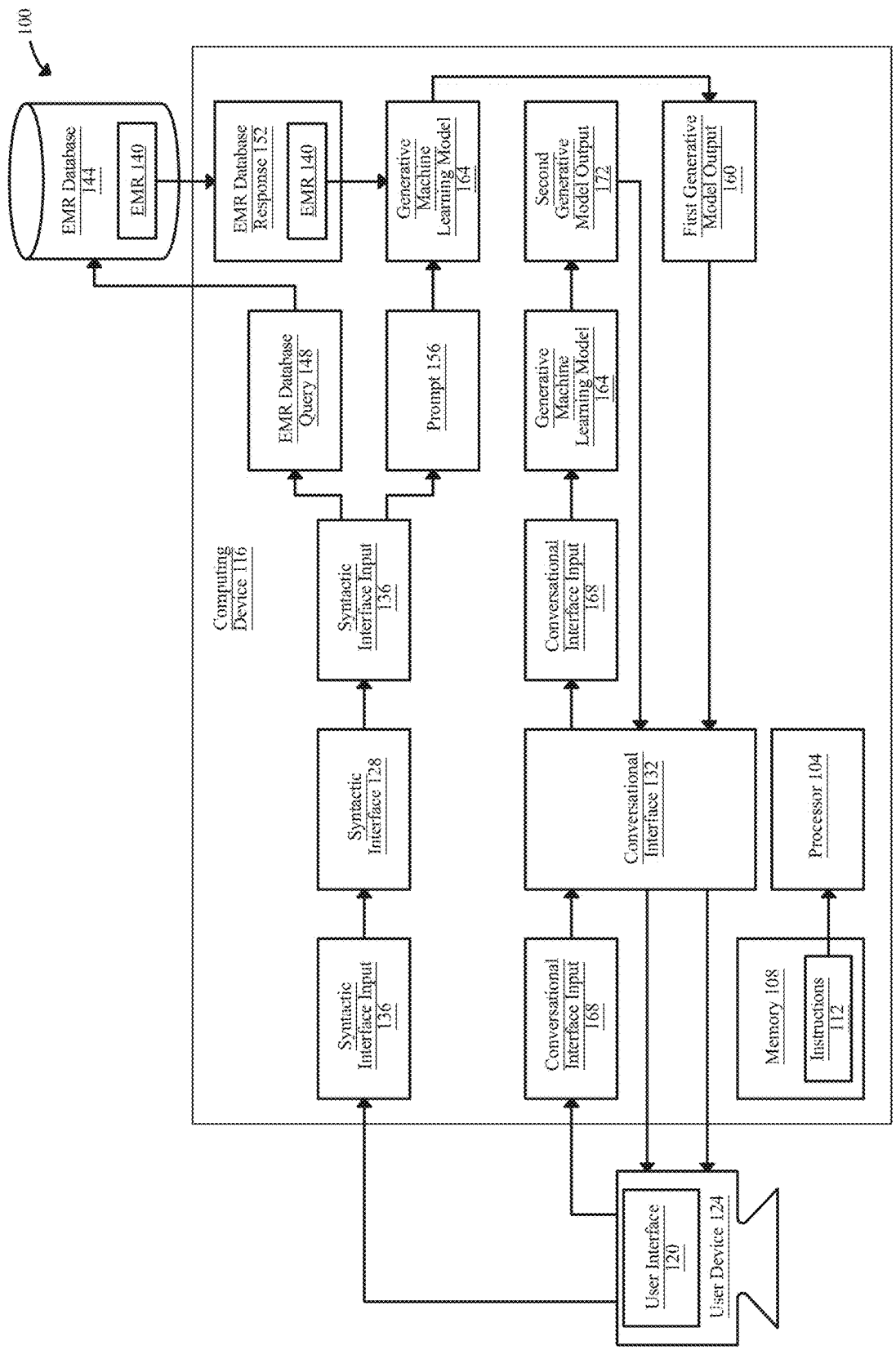
FIG. 1 is a diagram depicting an exemplary embodiment of an apparatus for configuring a generative machine learning model using a syntactic interface.

Referring now to FIG. 1, an exemplary embodiment of a system 100 for configuring a generative machine learning model using a syntactic interface is illustrated. System 100 may include a computing device 116. System 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 116 may include a single computing device operating independently, or may include two or more computing device operating in concert, in parallel, sequentially or the like; two or more computing devices may be included together in a single computing device or in two or more computing devices. Computing device 116 may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, system 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, system 100 includes user interface 120. User interface 120 may be a component of user device 124. User device 124 may include, in non-limiting examples, a smartphone, smartwatch, laptop computer, desktop computer, virtual reality device, or tablet. User interface 120 may include an input interface and/or an output interface. An input interface may include one or more mechanisms for a computing device to receive data from a user such as, in non-limiting examples, a mouse, keyboard, button, scroll wheel, camera, microphone, switch, lever, touchscreen, trackpad, joystick, and controller. An output interface may include one or more mechanisms for a computing device to output data to a user such as, in non-limiting examples, a screen, speaker, and haptic feedback system. An output interface may be used to display one or more elements of data described herein. As used herein, a device "displays" a datum if the device outputs the datum in a format suitable for communication to a user. For example, a device may display a datum by outputting text or an image on a screen or outputting a sound using a speaker.

Still referring to FIG. 1, in some embodiments, system 100 may display to a user syntactic interface 128. As used herein, a "syntactic interface" is a computer interface into which a user may input data using predefined syntax, a computer interface into which a user may input data of a specific data category, or both. In some embodiments, a syntactic interface may include a computer interface into which a user may input data using predefined syntax. For example, a slider which a user may interact with to indicate a minimum age of members of a cohort is a syntactic interface. In another example, a pair of buttons, one associated with biologically male subjects and the other associated with biologically female subjects, which a user may interact with to indicate which subjects are to be included in a cohort is a syntactic interface. In another example, a drop down menu in which a user may select from a list of drugs subjects of a cohort are to be on is a syntactic interface. In another example, a field which only accepts a number which a user may select and type a maximum age of members of a cohort is a syntactic interface. Additional examples of syntactic interfaces include drop down menus, sliders, radio buttons, and checkboxes. In some embodiments, a syntactic interface may include an interface element which allows a user to select one or more of a list of options.

In some embodiments, a syntactic interface may include a computer interface into which a user may input data of a specific data category. For example, a syntactic interface may accept, in text format, an address and/or a part of an address such as a country, state, or zip code. In another example, a syntactic interface may accept, in text format, a name of a medication, such as a trade name of a medication or a name of a drug included in a medication. In another example, a syntactic interface may accept, in text format, a list of one or more symptoms. In another example, a syntactic interface may accept, in text format, doctor's notes of a particular session between a doctor and a subject. In some embodiments, a syntactic interface may accept an input in a text format. In some embodiments, a syntactic interface may accept an input in an audio format. For example, a syntactic interface may include a button which a user may press and/or a field which a user may select, and the user may subsequently speak a name of a procedure into a microphone. In some embodiments, an input in an audio format may be transcribed to text using an automatic speech recognition system as described further below. In some embodiments, a syntactic interface may accept an input in an image format. For example, a user may input an image of handwritten doctor's notes of a particular session between a doctor and a subject, and these may be converted to text using an optical character recognition (OCR) function. A syntactic interface does not include an interface in which a user may input data in an unrestricted, freeform manner. For example, a field into which a user may input any prompt or question is not a syntactic interface.

Still referring to FIG. 1, in some embodiments, system 100 may display to a user conversational interface 132. As used herein, a "conversational interface" is a computer interface into which a user may input data, where the user is not restricted to use of predefined syntax. For example, a field which accepts freeform text input is a conversational interface. In another example, an interface which allows a user to input data by activating a microphone and speaking into the microphone is a conversational interface.

Still referring to FIG. 1, in some embodiments, system 100 may display syntactic interface 128 and/or conversational interface 132 using user interface 120. In some embodiments, syntactic interface 128 and/or conversational interface 132 may include a digital interface. In some embodiments, syntactic interface 128 and/or conversational interface 132 may include a graphical user interface (GUI).

In some embodiments, syntactic interface 128 and conversational interface 132 may be displayed simultaneously.

Still referring to FIG. 1, in some embodiments, system 100 receives syntactic interface input 136 from a user using a syntactic interface. As used herein, a "syntactic interface input" is a datum received by a computing device using a syntactic interface. In some embodiments, syntactic interface input 136 may include one or more data points which indicate qualities of a set of subjects whose data is to be retrieved. In some embodiments, syntactic interface input 136 may include one or more data points which indicate qualities of a set of subjects to be used to generate representative subject data and/or a synthesized subject datum. In a non-limiting example, syntactic interface input 136 may include a datum indicating that subjects are to be between the ages of 30 and 40.

Still referring to FIG. 1, in some embodiments, system 100 identifies electronic medical record (EMR) 140. System 100 may receive EMR 140 from EMR database 144.

System 100 may identify EMR 140 by generating EMR database query 148 as a function of syntactic interface input 136, querying EMR database 144 using EMR database query 148, and receiving from EMR database 144 EMR database response 152. As used herein, an "electronic medical record" or "EMR" is a data structure or data including medical data of a subject. An EMR may include, in non-limiting examples, an electrocardiogram (ECG) of a subject's heart, and narrative physician notes describing a subject's medical condition. As used herein, an "EMR database" is a set of one or more associated computing devices, where the set contains an EMR. As used herein, an "EMR database query" is a request for data which is sent to an EMR database. In some cases, an EMR database query may configure the EMR database to respond with an EMR. As used herein, an "EMR database response" is a query response which is sent by an EMR database in response to receipt of an EMR database query. In some embodiments, EMR database query 148 may be determined using a rule based system. For example, EMR database query 148 may be generated by inputting syntactic interface input 136 into an EMR database template segment, and such EMR database template segment may be selected using a rule based system as a function of syntactic interface input 136. In some embodiments, a rule based system may be used to determine which EMR database template segment to use. For example, an EMR database template segment may be selected based on a selection of a medical database, such that the chosen template generates an EMR database template segment which is compatible with the chosen database. In a non-limiting example, a rule based system may group medical databases by the format in which they accept requests for patient data and may select an EMR database template segment based on a group of a database to be searched. In some embodiments, a rule based system may determine whether to use a particular EMR database template segment as a function of whether syntactic interface input 136 indicates that a relevant feature is to be searched for. For example, entries into particular fields of syntactic interface 128 may be mapped to particular EMR database template segments which may be used to access specific entries in EMR database 144. In a non-limiting example, if syntactic interface input 136 specifies only that subjects are to be in a certain age range and on a certain medication, then EMR database template segments may be chosen which correspond to those features rather than, for example, biological sex. In another non-limiting example, if syntactic interface input 136 includes a feature indicating that subjects must be on a particular drug, then a rule based system may determine a EMR database template segment including a computer language indication as to whether or not a subject is on a particular drug. In some embodiments, multiple EMR database template segments may be combined in order to create EMR database query 148. EMR database query 148 may include, for example, a list of requirements of a cohort of patients, in a format readable by a computing device associated with EMR database 144. In some embodiments, the specific format used for an EMR database query 148 may depend on EMR database 144. For example, different EMR databases may require requests for information to be received in different formats. In some embodiments, EMR database 144 may provide information as to a format to provide EMR database query 148 in, and this format may be used. An EMR database query map may be used to generate EMR database query 148. As used herein, an "EMR database query map" is a predefined framework, a set of rules, or both that acts as a translator, intermediary, or both between a feature set and an EMR database query. In some embodiments, an EMR database query map may include instructions to apply one or more elements of syntactic interface input 136 to an EMR database template segment. For example, EMR database template segment may include a structure of an EMR database query in a format suitable for a particular EMR database, and such EMR database template segment may include specific locations into which variables of syntactic interface input 136 may be input. In a non-limiting example, syntactic interface input 136 may indicate a cohort of patients who are male and at least 20 years old. In this example, EMR database query map may include an EMR database template segment with a first location into which a feature to be searched by may be input, and system 100 may input into this location a datum associated with a subject's age. In this example, EMR database query map may include an EMR database template segment with a first location into which a datum indicating a mathematical relationship may be input, and system 100 may input into this location a datum associated with an age of a patient being greater than equal to an input age. In this example, EMR database query map may include an EMR database template segment with a first location into which a datum indicating a numerical value, and system 100 may input into this location a datum associated with the number 20.

Still referring to FIG. 1, in some embodiments, system 100 generates prompt 156 as a function of syntactic interface input 136. A prompt may include "promp" unspe a collection of data which indicates a datum desired by a user, a feature of a datum desired by a user, or both, and is in a format suitable for input into a generative machine learning model. Format of prompt 156 may depend on requirements of inputs of a machine learning model which prompt 156 is to be input into. In some embodiments, prompt 156 is a natural language prompt. As used herein, a "natural language prompt" is a prompt which is in a natural language format. System 100 may generate prompt 156 by inputting syntactic interface input 136 into a prompt template segment. A prompt template segment may be used to generate prompt 156 as described above with reference to EMR database template segment above.

Still referring to FIG. 1, in some embodiments, system 100 generates first generative model output 160 using a trained generative machine learning model 164. In some embodiments, system 100 may generate first generative model output 160 as a function of prompt 156 and EMR 140. In some embodiments, generative machine learning model 164 may include a large language model and/or first generative model output 160 may include a natural language output. In some embodiments, generative machine learning model 164 may be trained using unsupervised learning. In some embodiments, generative machine learning model 164 may include a language model, such as a large language model (LLM). In some embodiments, generative machine learning model 164 may accept as an input text data. In some embodiments, generative machine learning model 164 may accept as an input non-text data such as in non-limiting examples image data, video data, audio data, and/or data of a health record such as time series electrocardiogram (ECG) data. In some embodiments, generative machine learning model 164 may output data types including text, image, video, audio, and additional types of data as may be found in a health record. In some embodiments, generative machine learning model 164 may include a chatbot.

Still referring to FIG. 1, in some embodiments, a computing device may implement one or more aspects of "generative artificial intelligence," a type of artificial intelligence (AI) that uses machine learning algorithms to create, establish, or otherwise generate data such as, without limitation, first generative model output 160 and/or the like in any data structure as described herein (e.g., text, image, video, audio, among others) that is similar to one or more provided training examples. In an embodiment, machine learning module described herein may generate one or more generative machine learning models that are trained on one or more sets of training data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, a "generative model" refers to a statistical model of the joint probability distribution P(X, Y) on a given observable variable x, representing features or data that can be directly measured or observed and target variable y, representing the outcomes or labels that one or more generative models aims to predict or generate. For example, such variable x may include prompt 156 and/or EMR 140 and such variable y may include first generative model output 160.

Still referring to FIG. 1, in some cases, generative models may rely on Bayes theorem to find joint probability; for instance, and without limitation, Naïve Bayes classifiers may be employed by computing device to categorize input data.

Still referring to FIG. 1, in some embodiments, one or more generative machine learning models may include one or more Naïve Bayes classifiers generated, by computing device, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing Device may then calculate a likelihood table by calculating probabilities of different data entries and classification labels. Computing device may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as $P(X, Y)=P(Y)\Pi_i P(X_i| Y)$, wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of first generative model output 160 based on classification of prompt 156 and/or EMR 140, wherein the models may be trained using training data containing a plurality of features e.g., features of prompt 156 and/or EMR 140, and/or the like as input correlated to a plurality of labeled classes as output.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 4.

Still referring to FIG. 1, in some embodiments, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 4 to distinguish between different categories such as real vs fake or correct vs incorrect, or states such as TRUE vs. FALSE within the context of generated data such as, without limitations, first generative model output 160, and/or the like. In some cases, computing device may implement one or more classification algorithms such as, without limitation, Support Vector Machines (SVM), Logistic Regression, Decision Trees, and/or the like to define decision boundaries.

Still referring to FIG. 1, in some embodiments, generator of GAN may be responsible for creating synthetic data that resembles real first generative model output 160. In some cases, GAN may be configured to receive prompt 156 and/or EMR 140 as input and generates corresponding first generative model output 160 containing information describing or evaluating the performance of one or more instances of prompt 156 and/or EMR 140. On the other hand, discriminator of GAN may evaluate the authenticity of the generated content by comparing it to real first generative model output 160, for example, discriminator may distinguish between genuine and generated content and providing feedback to generator to improve the model performance.

Still referring to FIG. 1, in some embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

Still referring to FIG. 1, in some embodiments, VAE may be used by computing device to model complex relationships between prompt 156 and/or EMR 140. In some cases, VAE may encode input data into a latent space, capturing first generative model output 160. Such encoding process may include learning one or more probabilistic mappings from observed prompt 156 and/or EMR 140 to a lower-dimensional latent representation. Latent representation may then be decoded back into the original data space, therefore reconstructing the prompt 156 and/or EMR 140. In some cases, such decoding process may allow VAE to generate new examples or variations that are consistent with the learned distributions.

Still referring to FIG. 1, in some embodiments, one or more generative machine learning models may utilize one or more predefined templates representing, for example, and without limitation, correct first generative model output 160. In a non-limiting example, one or more templates (i.e., predefined models or representations of correct and ideal first generative model output 160) may serve as benchmarks for comparing and evaluating prompt 156 and/or EMR 140.

Still referring to FIG. 1, computing device may configure generative machine learning models to analyze input data to one or more predefined templates, thereby allowing computing device to identify discrepancies or deviations from a desired form of first generative model output 160. In some cases, computing device may be configured to pinpoint specific errors in prompt 156 and/or EMR 140. In a non-limiting example, computing device may be configured to implement generative machine learning models to incorporate additional models to detect additional instances of prompt 156 and/or EMR 140. In some cases, errors may be classified into different categories or severity levels. In a non-limiting example, some errors may be considered minor, and generative machine learning model such as, without limitation, GAN may be configured to generate first generative model output 160 contain only slight adjustments while others may be more significant and demand more substantial corrections. In some embodiments, computing device may be configured to flag or highlight an error in input data and computing device may edit prompt 156 and/or EMR 140 using one or more generative machine learning models described herein. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 1, in some cases, computing device may be configured to identify, and rank detected common deficiencies across a plurality of data sources; for instance, and without limitation, one or more machine learning models may classify errors in a specific order such as by ranking deficiencies in a descending order of commonality. Such ranking process may enable a prioritization of most prevalent issues, allowing instructors or computing device to address the issue.

Still referring to FIG. 1, in some cases, one or more generative machine learning models may also be applied by computing device to edit, modify, or otherwise manipulate existing data or data structures. In an embodiment, output of training data used to train one or more generative machine learning models such as GAN as described herein may include training data that linguistically or visually demonstrate modified prompt 156 and/or EMR 140. In some cases, first generative model output 160 may be synchronized with prompt 156 and/or EMR 140. In some cases, such first generative model output 160 may be integrated with the prompt 156 and/or EMR 140, offering a user a multisensory instructional experience.

Still referring to FIG. 1, computing device may be configured to continuously monitor prompt 156 and/or EMR 140. In an embodiment, computing device may configure discriminator to provide ongoing feedback and further corrections as needed to subsequent input data. In some cases, one or more sensors such as, without limitation, wearable device, motion sensor, or other sensors or devices described herein may provide additional prompt 156 and/or EMR 140 that may be used as subsequent input data or training data for one or more generative machine learning models described herein.

Still referring to FIG. 1, other exemplary embodiments of generative machine learning models may include, without limitation, long short-term memory networks (LSTMs), (generative pre-trained) transformer (GPT) models, mixture density networks (MDN), and/or the like.

Still referring to FIG. 1, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate first generative model output 160. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others.

Still referring to FIG. 1, in some embodiments, generative machine learning model 164 may include a language model, such as an LLM. As used herein, a "language model" is a program capable of interpreting natural language, generating natural language, or both. In some embodiments, a language model may be configured to interpret the output of an automatic speech recognition function and/or an OCR function. A language model may include a neural network. A language model may be trained using a dataset that includes natural language.

Still referring to FIG. 1, in some embodiments, a language model may be configured to extract one or more words from a document. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols. Textual data may be parsed into tokens, which may include a simple word (sequence of letters separated by whitespace) or more generally a sequence of characters. As used herein, a "token," is a smaller, individual grouping of text from a larger source of text. Tokens may be broken up by word, pair of words, sentence, or other delimitations. Tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as chains, for example for use as a Markov chain or Hidden Markov Model.

Still referring to FIG. 1, generating language model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, processor 104 may determine one or more language elements in prompt 156 and/or EMR 140 by identifying and/or detecting associations between one or more language elements (including phonemes or phonological elements, morphemes or morphological elements, syntax or syntactic elements, semantics or semantic elements, and pragmatic elements) extracted from at least prompt 156 and/or EMR 140, including without limitation mathematical associations, between such words. Associations between language elements and relationships of such categories to other such term may include, without limitation, mathematical associations, including without limitation statistical correlations between any language element and any other language element and/or Language elements. Processor 104 may compare an input such as a sentence from prompt 156 and/or EMR 140 with a list of keywords or a dictionary to identify language elements. For example, processor 104 may identify whitespace and punctuation in a sentence and extract elements comprising a string of letters, numbers or characters occurring adjacent to the whitespace and punctuation. Processor 104 may then compare each of these with a list of keywords or a dictionary. Based on the determined keywords or meanings associated with each of the strings, processor 104 may determine an association between one or more of the extracted strings and a feature of a subject and/or set of subjects, such as an association between the word "insulin" and a subject having diabetes. Associations may take the form of statistical correlations and/or mathematical associations, which may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory.

Still referring to FIG. 1, processor 104 may be configured to determine one or more language elements in prompt 156 and/or EMR 140 using machine learning. For example, processor 104 may generate the language processing model by any suitable method, including without limitation a natural language processing classification algorithm; language processing model may include a natural language process classification model that enumerates and/or derives statistical relationships between input terms and output terms. An algorithm to generate language processing model may include a stochastic gradient descent algorithm, which may include a method that iteratively optimizes an objective function, such as an objective function representing a statistical estimation of relationships between terms, including relationships between input language elements and output patterns or conversational styles in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word, phrase, and/or other semantic unit. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Still referring to FIG. 1, processor 104 may be configured to determine one or more language elements in prompt 156 and/or EMR 140 using machine learning by first creating or receiving language classification training data. Training data may include data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, language classification training data may be a training data set containing associations between language element inputs and associated language element outputs. Language element inputs and outputs may be categorized by communication form such as written language elements, spoken language elements, typed language elements, or language elements communicated in any suitable manner. Language elements may be categorized by component type, such as phonemes or phonological elements, morphemes or morphological elements, syntax or syntactic elements, semantics or semantic elements, and pragmatic elements. Associations may be made between similar communication types of language elements (e.g. associating one written language element with another written language element) or different language elements (e.g. associating a spoken language element with a written representation of the same language element). Associations may be identified between similar communication types of two different language elements, for example written input consisting of the syntactic element "that" may be associated with written phonemes/th/,/ă/, and/t/. Associations may be identified between different communication forms of different language elements. For example, the spoken form of the syntactic element "that" and the associated written phonemes above. Language classification training data may be created using a classifier such as a language classifier. An exemplary classifier may be created, instantiated, and/or run using processor 104, or another computing device. Language classification training data may create associations between any type of language element in any format and other type of language element in any format. Additionally, or alternatively, language classification training data may associate language element input data to a feature related to a subject and/or set of subjects and/or data to be produced. For example, language classification training data may associate occurrences of the syntactic elements "generate," "a", and "cohort" in a single sentence with the functionality of assembling a set of EMR of subjects.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)÷P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Still referring to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, language processing module may use a corpus of documents to generate associations between language elements in a language processing module, and a diagnostic engine may then use such associations to analyze words extracted from one or more documents and determine that the one or more documents indicate significance of a category. In an embodiment, a computing device may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into a computing device. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still referring to FIG. 1, a language model may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

Still referring to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

Still referring to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Alzheimer's disease risk among 20-30 year old patients is", then it may be highly likely that the word "low" will come next. An LLM may output such predictions by ranking words by likelihood or a prompt parameter. For the example given above, an LLM may score "low" as the most likely, "lower" as the next most likely, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

Still referring to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

Still referring to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

Still referring to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a nonlimiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referring to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

Still referring to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Still referring to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

Still referring to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

Still referring to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

Still referring to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Still referring to FIG. 1, in some embodiment, decoder may be stacked N layers high, with each layer taking in inputs from the encoder and layers before it. Stacking layers may allow an LLM to learn to extract and focus on different combinations of attention from its attention heads.

Still referring to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with EMR of a subject.

Still referring to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Still referring to FIG. 1, in some embodiments, system 100 uses conversational interface 132 to display first generative model output 160 to a user. In some embodiments, display of first generative model output 160 may be implemented by generation of a visual element and/or visual element data structure as a function of first generative model output 160 and display of such visual element. In some embodiments, a visual element data structure may include a visual element. As used herein, a "visual element" is a datum that is displayed visually to a user. In some embodiments, a visual element data structure may include a rule for displaying visual element. In some embodiments, a visual element data structure may be determined as a function of first generative model output 160. In some embodiments, a visual element data structure may be determined as a function of an item from the list consisting of syntactic interface input 136, EMR database query 148, syntactic interface 128, EMR 140, prompt 156, first generative model output 160, conversational interface 132, conversational interface input 168, and second generative model output 172. In a non-limiting example, a visual element data structure may be generated such that visual element describing or highlighting first generative model output 160 is displayed to a user. In another example, a list of EMR retrieved from EMR database 144 may be displayed to a user.

Still referring to FIG. 1, in some embodiments, visual element may include one or more elements of text, images, shapes, charts, particle effects, interactable features, and the like. For example, syntactic interface 128 and/or conversational interface 132 may include one or more interactable features.

Still referring to FIG. 1, a visual element data structure may include rules governing if or when visual element is displayed. In a non-limiting example, a visual element data structure may include a rule causing a visual element describing first generative model output 160 to be displayed when a user selects first generative model output 160 using a graphical user interface (GUI).

Still referring to FIG. 1, a visual element data structure may include rules for presenting more than one visual element, or more than one visual element at a time. In an embodiment, about 1, 2, 3, 4, 5, 10, 20, or 50 visual elements are displayed simultaneously.

Still referring to FIG. 1, a visual element data structure rule may apply to a single visual element or datum, or to more than one visual element or datum. For example, a visual element data structure may rank visual elements and/or other data and/or apply numerical values to them, and a computing device may display a visual element as a function of such rankings and/or numerical values. A visual element data structure may apply rules based on a comparison between such a ranking or numerical value and a threshold. For example, rankings for elements of syntactic interface 128 may depend on which elements of syntactic interface 128 a user has already interacted with.

Still referring to FIG. 1, in some embodiments, visual element may be interacted with. For example, visual element may include an interface, such as a button or menu. In some embodiments, visual element may be interacted with using a user device such as a smartphone.

Still referring to FIG. 1, in some embodiments, system 100 may transmit visual element data structure to user device 124. In some embodiments, visual element data structure may configure user device 124 to display visual element. In some embodiments, visual element data structure may cause an event handler to be triggered in an application of user device 124 such as a web browser. In some embodiments, triggering of an event handler may cause a change in an application of user device 124 such as display of visual element.

Still referring to FIG. 1, in some embodiments, system 100 may transmit visual element to a display. A display may communicate visual element to user. A display may include, for example, a smartphone screen, a computer screen, or a tablet screen. A display may be configured to provide a visual interface. A visual interface may include one or more virtual interactive elements such as, without limitation, buttons, menus, and the like. A display may include one or more physical interactive elements, such as buttons, a computer mouse, or a touchscreen, that allow user to input data into the display. Interactive elements may be configured to enable interaction between a user and a computing device. In some embodiments, a visual element data structure is determined as a function of data input by user into a display.

Still referring to FIG. 1, a variable and/or datum described herein may be represented using a data structure. In some embodiments, a data structure may include one or more functions and/or variables, as a class might in object-oriented programming. In some embodiments, a data structure may include data in the form of a Boolean, integer, float, string, date, and the like. In a non-limiting example, a prompt data structure may include a string value representing text to be input into generative machine learning model 164. In some embodiments, data in a data structure may be organized in a linked list, tree, array, matrix, tenser, and the like. In some embodiments, a data structure may include or be associated with one or more elements of metadata. A data structure may include one or more self-referencing data elements, which processor 104 may use in interpreting the data structure. In a non-limiting example, a data structure may include "<date>" and "</date>," tags, indicating that the content between the tags is a date.

Still referring to FIG. 1, a data structure may be stored in, for example, memory 108 or a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, in some embodiments, a data structure may be read and/or manipulated by processor 104. In a non-limiting example, a prompt data structure may be read and input into generative machine learning model 164.

Still referring to FIG. 1, in some embodiments, data contained within a data structure may be calibrated. In some embodiments, such data may be trained using a machine learning algorithm. In a non-limiting example, a data structure may include an array of data representing the weights of a neural network. In this example, the neural network may be trained on a set of training data, and a back propagation algorithm may be used to modify the data in the array. In some embodiments, application of a back propagation algorithm may involve computing a gradient of a loss function based on the weights of a neural network, and modifying the weights based on the gradient. Machine learning models and neural networks are described further herein.

Still referring to FIG. 1, in some embodiments, system 100 may receive conversational interface input 168 from a user using conversational interface 132. As used herein, a "conversational interface input" is a datum received by a computing device from a user using a conversational interface. In some embodiments, conversational interface input 168 may include one or more data points which indicate qualities of a set of subjects whose data is to be retrieved. In some embodiments, conversational interface input 168 may include one or more data points which indicate qualities of a set of subjects to be used to generate representative subject data and/or a synthesized subject datum. Conversational interface input 168 may include, in non-limiting examples, a question based on first generative model output 160, a request to modify first generative model output 160, and a request to generate a new output based on a different set of EMR. In some embodiments, conversational interface input 168 may be used to generate second generative model output 172 using generative machine learning model 164. In some embodiments, second generative model output 172 may be displayed to a user as described above in the context of first generative model output 160.

Still referring to FIG. 1, in some embodiments, system 100 may collect conversational interface input 168 in the form of audio data including speech, and such audio data may be processed using automatic speech recognition. In some embodiments, automatic speech recognition may require training (i.e., enrollment). In some cases, training an automatic speech recognition model may require an individual speaker to read text or isolated vocabulary. In some cases, speech training data may include an audio component having an audible verbal content, the contents of which are known a priori by a computing device. Computing device may then train an automatic speech recognition model according to training data which includes audible verbal content correlated to known content. In this way, computing device may analyze a person's specific voice and train an automatic speech recognition model to the person's speech, resulting in increased accuracy. Alternatively, or additionally, in some cases, computing device may include an automatic speech recognition model that is speaker independent. As used in this disclosure, a "speaker independent" automatic speech recognition process is an automatic speech recognition process that does not require training for each individual speaker. Conversely, as used in this disclosure, automatic speech recognition processes that employ individual speaker specific training are "speaker dependent".

Still referring to FIG. 1, in some embodiments, an automatic speech recognition process may perform voice recognition or speaker identification. As used in this disclosure, "voice recognition" is a process of identifying a speaker, from audio content, rather than what the speaker is saying. In some cases, computing device may first recognize a speaker of verbal audio content and then automatically recognize speech of the speaker, for example by way of a speaker dependent automatic speech recognition model or process. In some embodiments, an automatic speech recognition process can be used to authenticate or verify an identity of a speaker. In some cases, a speaker may or may not include subject. For example, subject may speak within audio data, but others may speak as well.

Still referring to FIG. 1, in some embodiments, an automatic speech recognition process may include one or all of acoustic modeling, language modeling, and statistically based speech recognition algorithms. In some cases, an automatic speech recognition process may employ hidden Markov models (HMMs). As discussed in greater detail below, language modeling such as that employed in natural language processing applications like document classification or statistical machine translation, may also be employed by an automatic speech recognition process.

Still referring to FIG. 1, an exemplary algorithm employed in automatic speech recognition may include or even be based upon hidden Markov models. Hidden Markov models (HMMs) may include statistical models that output a sequence of symbols or quantities. HMMs can be used in speech recognition because a speech signal can be viewed as a piecewise stationary signal or a short-time stationary signal. For example, over a short time scale (e.g., 10 milliseconds), speech can be approximated as a stationary process. Speech (i.e., audible verbal content) can be understood as a Markov model for many stochastic purposes.

Still referring to FIG. 1, in some embodiments HMMs can be trained automatically and may be relatively simple and computationally feasible to use. In an exemplary automatic speech recognition process, a hidden Markov model may output a sequence of n-dimensional real-valued vectors (with n being a small integer, such as 10), at a rate of about one vector every 10 milliseconds. Vectors may consist of cepstral coefficients. A cepstral coefficient requires using a spectral domain. Cepstral coefficients may be obtained by taking a Fourier transform of a short time window of speech yielding a spectrum, decorrelating the spectrum using a cosine transform, and taking first (i.e., most significant) coefficients. In some cases, an HMM may have in each state a statistical distribution that is a mixture of diagonal covariance Gaussians, yielding a likelihood for each observed vector. In some cases, each word, or phoneme, may have a different output distribution; an HMM for a sequence of words or phonemes may be made by concatenating an HMMs for separate words and phonemes.

Still referring to FIG. 1, in some embodiments, an automatic speech recognition process may use various combinations of a number of techniques in order to improve results. In some cases, a large-vocabulary automatic speech recognition process may include context dependency for phonemes. For example, in some cases, phonemes with different left and right context may have different realizations as HMM states. In some cases, an automatic speech recognition process may use cepstral normalization to normalize for different speakers and recording conditions. In some cases, an automatic speech recognition process may use vocal tract length normalization (VTLN) for male-female normalization and maximum likelihood linear regression (MLLR) for more general speaker adaptation. In some cases, an automatic speech recognition process may determine so-called delta and delta-delta coefficients to capture speech dynamics and might use heteroscedastic linear discriminant analysis (HLDA). In some cases, an automatic speech recognition process may use splicing and a linear discriminate analysis (LDA)-based projection, which may include heteroscedastic linear discriminant analysis or a global semi-tied covariance transform (also known as maximum likelihood linear transform [MLLT]). In some cases, an automatic speech recognition process may use discriminative training techniques, which may dispense with a purely statistical approach to HMM parameter estimation and instead optimize some classification-related measure of training data; examples may include maximum mutual information (MMI), minimum classification error (MCE), and minimum phone error (MPE).

Still referring to FIG. 1, in some embodiments, an automatic speech recognition process may be said to decode speech (i.e., audible verbal content). Decoding of speech may occur when an automatic speech recognition system is presented with a new utterance and must compute a most likely sentence. In some cases, speech decoding may include a Viterbi algorithm. A Viterbi algorithm may include a dynamic programming algorithm for obtaining a maximum a posteriori probability estimate of a most likely sequence of hidden states (i.e., Viterbi path) that results in a sequence of observed events. Viterbi algorithms may be employed in context of Markov information sources and hidden Markov models. A Viterbi algorithm may be used to find a best path, for example using a dynamically created combination hidden Markov model, having both acoustic and language model information, using a statically created combination hidden Markov model (e.g., finite state transducer [FST] approach).

Still referring to FIG. 1, in some embodiments, speech (i.e., audible verbal content) decoding may include considering a set of good candidates and not only a best candidate, when presented with a new utterance. In some cases, a better scoring function (i.e., re-scoring) may be used to rate each of a set of good candidates, allowing selection of a best candidate according to this refined score. In some cases, a set of candidates can be kept either as a list (i.e., N-best list approach) or as a subset of models (i.e., a lattice). In some cases, re-scoring may be performed by optimizing Bayes risk (or an approximation thereof). In some cases, re-scoring may include optimizing for sentence (including keywords) that minimizes an expectancy of a given loss function with regards to all possible transcriptions. For example, re-scoring may allow selection of a sentence that minimizes an average distance to other possible sentences weighted by their estimated probability. In some cases, an employed loss function may include Levenshtein distance, although different distance calculations may be performed, for instance for specific tasks. In some cases, a set of candidates may be pruned to maintain tractability.

Still referring to FIG. 1, in some embodiments, an automatic speech recognition process may employ dynamic time warping (DTW)-based approaches. Dynamic time warping may include algorithms for measuring similarity between two sequences, which may vary in time or speed. For instance, similarities in walking patterns would be detected, even if in one video the person was walking slowly and if in another he or she were walking more quickly, or even if there were accelerations and deceleration during the course of one observation. DTW has been applied to video, audio, and graphics-indeed, any data that can be turned into a linear representation can be analyzed with DTW. In some cases, DTW may be used by an automatic speech recognition process to cope with different speaking (i.e., audible verbal content) speeds. In some cases, DTW may allow computing device to find an optimal match between two given sequences (e.g., time series) with certain restrictions. That is, in some cases, sequences can be "warped" non-linearly to match each other. In some cases, a DTW-based sequence alignment method may be used in context of hidden Markov models.

Still referring to FIG. 1, in some embodiments, an automatic speech recognition process may include a neural network. Neural network may include any neural network, for example those disclosed with reference to FIGS. 4-6. In some cases, neural networks may be used for automatic speech recognition, including phoneme classification, phoneme classification through multi-objective evolutionary algorithms, isolated word recognition, audiovisual speech recognition, audiovisual speaker recognition and speaker adaptation. In some cases, neural networks employed in automatic speech recognition may make fewer explicit assumptions about feature statistical properties than HMMs and therefore may have several qualities making them attractive recognition models for speech recognition. When used to estimate the probabilities of a speech feature segment, neural networks may allow discriminative training in a natural and efficient manner. In some cases, neural networks may be used to effectively classify audible verbal content over short-time interval, for instance such as individual phonemes and isolated words. In some embodiments, a neural network may be employed by automatic speech recognition processes for pre-processing, feature transformation and/or dimensionality reduction, for example prior to HMM-based recognition. In some embodiments, long short-term memory (LSTM) and related recurrent neural networks (RNNs) and Time Delay Neural Networks (TDNN's) may be used for automatic speech recognition, for example over longer time intervals for continuous speech recognition.

Figure 2:
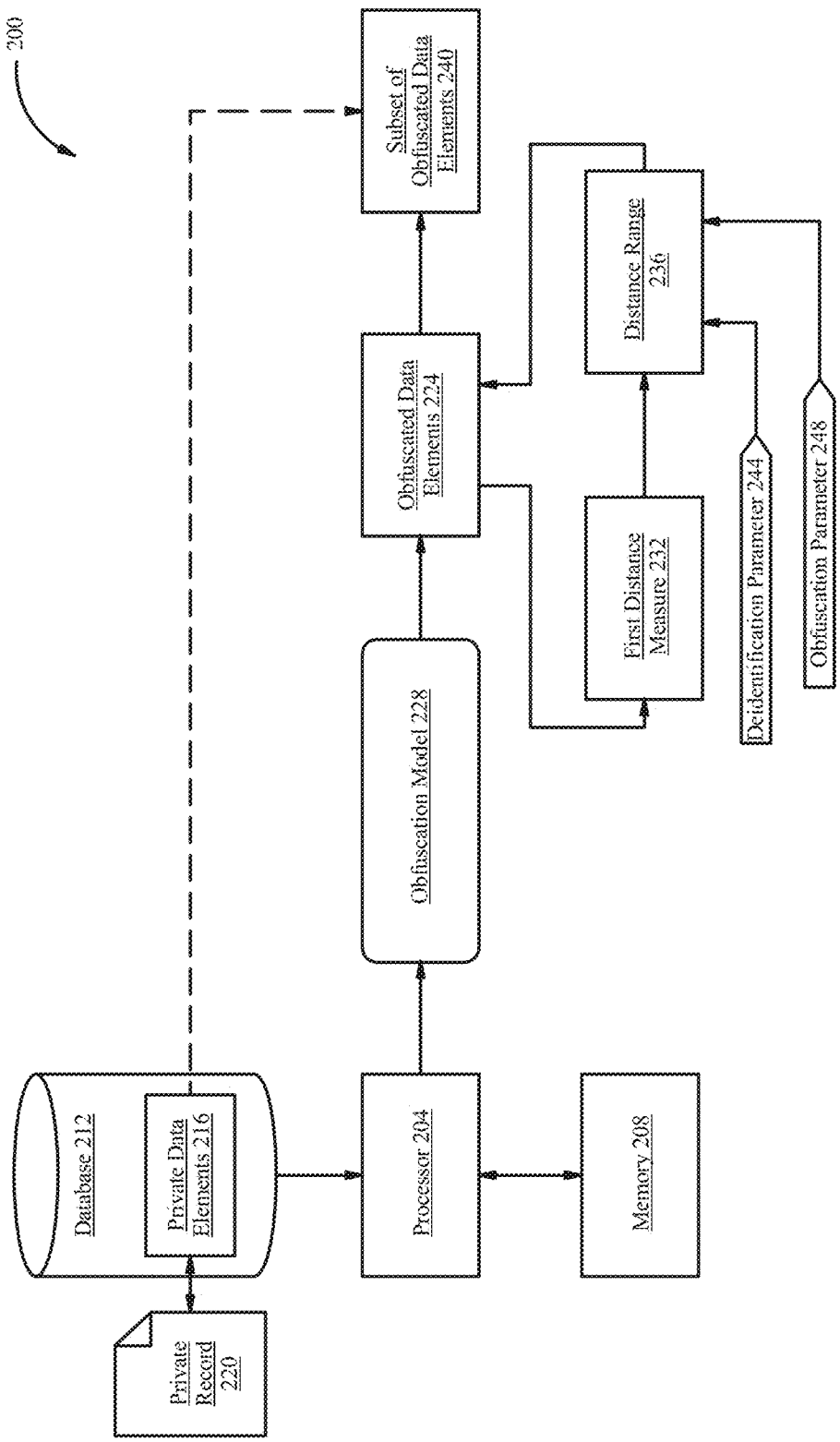
FIG. 2 is a diagram of an apparatus for generating obfuscated data elements within a computing environment.

Still referring to FIG. 2, in some embodiments, an EMR database response may include a plurality of private data elements belonging to at least a private record; and generating a generative model output may include generating, using a generative machine learning model, a set of obfuscated data elements representative of the at least a private record, as a function of the plurality of private data elements. In some embodiments, a computing device may determine a first distance measure between at least an obfuscated data element within the set of obfuscated data elements and at least a private data element of the plurality of private data elements within the database; and verify, for the at least an obfuscated data element within the set of obfuscated data elements, the first distance measure is within a distance range, wherein a minimum threshold of the distance range is determined as a function of a deidentification parameter; and a maximum threshold of the distance range is determined as a function of an obfuscation parameter. In some embodiments, a computing device may be further configured to fine-tune a generative machine learning model on a subset of private data elements selected from the plurality of private data elements within the database corresponding to at least one pre-determined domain. In some embodiments, generating a set of obfuscated data elements may include sampling from a noise distribution on a deidentified version of the plurality of private data elements.

Still referring to FIG. 2, an exemplary embodiment of an apparatus 200 for generating obfuscated data elements within a computing environment is illustrated. Apparatus 200 may include processor 204 and/or memory 208. Processor 204 may be configured to access a database 212 containing a plurality of private data elements 216 belonging to at least a private record 220. A database may include a collection of data that can be accessed, managed, and updated. In one or more embodiments, database 212 may include one or more systematically organized collections of a plurality of private records as described in further detail below, interfacing with processor 204 and one or more other data storage mechanisms, which may be efficiently retrieved, updated, and/or manipulated. As a non-limiting example, database 212 as described herein may include a relational database having one or more structured formats that organize plurality of private data elements 216 into one or more tables with plurality of rows and columns. Apparatus 200 may implement one or more aspect of a database management system (DBMS), for example and without limitation, functions such as data element insertion, querying, update, delete, and administration may be implemented and performed, by processor 204, on database 212. In some embodiments, database 212 may include flexible schemas e.g., key-value stores. In some cases, processor 204 may access one or more data warehouses or data lakes or repositories that report data analytics or hold a large amount of raw data in its native format until needed. Additionally, or alternatively, database 212 may include one or more datasets or "corpora," collections of values, written texts, recorded speech, or the like, for example, and without limitation, one or more electronic health record (EHR) as described in further detail below. Other exemplary embodiments of database 212 as described herein may include, without limitation, financial transaction logs, social media content datasets, linguistic corpora, among others.

With continued reference to FIG. 2, as a non-limiting example, database 212 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records such as, without limitation, plurality of private data elements 216 as described in further detail below. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database 212 may store, retrieve, organize, and/or reflect data elements as used herein, as well as categories and/or populations of data consistently with this disclosure.

With continued reference to FIG. 2, as used in this disclosure, a "data element" is a unit of data that represents a single piece of information defined in a way that is understandable and usable. In an embodiment, data element may be an atomic unit of database 212 (e.g., dataset) or a data structure, which cannot be broken down into smaller parts without losing its meaning or value. In some cases, data elements may be numerical, textural, binary, or any other type of data that can be stored, processed, and retrieved by processor 204. In some cases, data element may include one or more data attributes, such as, without limitation, a name, a value, a data type, and/or a set of metadata that describes data element's properties, constraints, or relationships with other data elements. A "private data element," for the purpose of this disclosure, is a data element that is associated with an individual or entity that requires protection from unauthorized access or disclosure. In some cases, private data element may include any initial or original data element that is an unaltered and stored within database 212 before any processing, transformation, or obfuscation as described herein has been applied. A "private record," as used herein, is a collection of private data elements. In one or more embodiments, plurality of private data elements may include raw, authentic data collected from one or more private records e.g., EHRs, financial transaction logs, user behavior data, sensor data, PII, among others. As a non-limiting example, plurality of private data elements 216 may include sensitive information, regulated data, and/or any data under access control. In some cases, plurality of private data elements may be subject of obfuscation as described herein to protect sensitive information from unauthorized access while still allowing for meaningful use (e.g., predictive modeling to improve patient outcomes, financial risk assessment, and/or the like) of the data in aggregated or anonymized form.

With continued reference to FIG. 2, in some cases, each private data element of plurality of private data elements 216 and/or at least a private record 220 may be represented as a vector. In these cases, database 212 containing plurality of private data elements 216, such as, without limitation, a corpus, may be represented as a vector space. A may include a data structure that represents one or more a quantitative values and/or measures of a given data element. A vector may be represented as an n-tuple of values, where n is one or more values, as described in further detail below. A "vector space," as defined in his disclosure, is a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. In some cases, each dimension may correspond to a feature of the data. In some cases, at least a private record 220 such as, without limitation, a patient's health record may describe one or more data fields (i.e., plurality of private data elements 216) such as, without limitation, age, weight, blood pressure readings, cholesterol level, and the like.

With continued reference to FIG. 2, in an embodiment, database 212 may include a collection of vectors as described above. As a non-limiting example, database 212 may include a plurality of text documents, wherein each document of the plurality of text documents may be transformed into a vector using TF-IDF or word embeddings. In some cases, each dimension in each vector may represent, for example, a significance of a word or phrase within the corresponding document in the context of the entire database 212. In some cases, two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes. Processor 204 may be configured to perform searching, classification, topic modeling, content generation, and/or the like on such text data stored in database 212.

With continued reference to FIG. 2, in one or more embodiments, processor 204 may perform determinations, classification, and/or analysis steps, methods, processes, or the like as described in this disclosure using machine-learning processes trained on database 212. A machine-learning process may include a process that automatedly uses a body of data known as "training data" and/or a "training set" to generate an algorithm that will be performed by a processor/module to produce outputs given data provided as inputs; this is in contrast to a non-machine learning software program where the commands to be executed are determined in advance by a user and written in a programming language. Machine-learning process may utilize supervised, unsupervised, lazy-learning processes and/or neural networks, described further below. As a non-limiting example, one or more machine learning models as described in further detail below may be trained on plurality of private data elements 216 within database 212. For instance, a neural network may be trained on plurality of private data elements containing medical imaging data with labels, learn and predict health-related outcomes e.g., presence of diseases or the effectiveness of certain treatments.

With continued reference to FIG. 2, processor 204 is configured to generate a set of obfuscated data elements 224, representative of at least a private record 220, as a function of plurality of private data elements 216. As used in this disclosure, "obfuscated data elements" are data elements that have been intentionally modified or transformed from its original state. In some cases, obfuscated data elements may preserve a pre-determined level of utility that allows for specific uses of the data elements. In some cases, plurality of private data elements 216 may be transformed into a plurality of obfuscated data elements to prevent unauthorized access to, or disclosure of sensitive information; for instance, and without limitation, each obfuscated data element may no longer directly or indirectly reveal sensitive details but may still support processor 204 to perform data analysis, testing, or other operational processes as described herein without compromising its confidentiality. As another non-limiting example, obfuscated data element may include a synthetic data element. In some cases, set of obfuscated data elements may include one or more preliminary obfuscated data elements, wherein the "preliminary obfuscated data elements," for the purpose of this disclosure, are initial or general obfuscated data elements that have been processed or transformed from their original state to a modified state but require further refinement, evaluation, and/or adjustment to meet pre-defined privacy, security, or utility criteria before considered as "finalized obfuscated data elements" as described further below. In one or more embodiments, obfuscated data may be generated through one or more methods of distortion, encryption, or other transformation techniques as described below to make plurality of private data elements 216 within database 212 unintelligible and/or unattributable to specific individuals or entities without losing data's utility for certain applications or analyses, such as, without limitation, machine learning model training, data analytics, secure data sharing, and/or the like. Exemplary obfuscated data elements may include, without limitation, encrypted email content, masked customer records, generated medical data, anonymized survey data, tokenized payment transactions, and the like.

With continued reference to FIG. 2, as a non-limiting example, obfuscated data elements may include data elements describing generic placeholders or tokens, pseudonyms, presumptions, or hypothesis, and/or the like. In some cases, generating set of obfuscated data elements 224 may include replacing one or more private identifiers (i.e., specific pieces of information that can directly or indirectly identify an individual, such as names, social security numbers, addresses, email addresses, and/or the like) with one or more pseudonyms or placeholders. Data subsequent to such replacement may be matched with plurality of private data elements 216 without revealing actual source identity. In some cases, plurality of obfuscated data elements may be reversible with additional information, for example, and without limitation, through the use of a secure mapping database that may be configured to store relationships between the pseudonyms and the private data elements. In some cases, plurality of private data elements 216 within database 212 may be hidden with one or more altered values. In an embodiment, processor 204 may statically mask one or more private data elements of plurality of private data elements in database 212 by permanently substituting the one or more private data elements with masked version data elements before plurality of private data elements leaves the server or database 212 or before it is used in a less secure applications or testing computing environment. In another embodiment, processor may temporarily mask one or more private data elements of plurality of private data elements in real-time during access or query operations. As a non-limiting example, when a request to view or process plurality of private data elements 216 is made, sensitive information may be automatically masked to the user based on the user's access level, wherein plurality of private data elements may remain intact and unaltered within database 212.

With continued reference to FIG. 2, in some cases, one or more "tokens" or "placeholders" (i.e., non-sensitive equivalent) may be generated by processor 204 to replace sensitive elements within each private data element of plurality of private data elements 216 using a secure tokenization module. As used in this disclosure, a "secure tokenization module" is a specialized component or piece of software designed to systematically convert sensitive data elements into a non-sensitive representation, referred to as tokens, which have no exploitable value or meaning outside the system. In one or more embodiments, secure tokenization module may map tokens or placeholders within one or more obfuscated data elements back to the original data through secure tokenization module. In one or more embodiments, secure tokenization module may be configured to securely remove specific data elements or part of data element e.g., identifying details to prevent obfuscated data element from being traced back to one or more individuals. For example, K-anonymity may be implemented, where private data elements may be modified until each private data element is indistinguishable from at least k−1 other data elements in database 212. In some cases, generating set of obfuscated data elements may include aggregating plurality of private data elements 216, where individual private data element may be summarized into one or more larger groups of data elements using secure tokenization module.

With continued reference to FIG. 2, as a non-limiting example, a private data element e.g., a sequence of social security numbers associated with a customer within database 212 may be replaced, by secure tokenization module, with a series of "X's" or a random set of numbers, effectively obscuring the private data element. Such replacement may be permanent, meaning private data element may never be displayed to developers or testers. As another non-limiting example, when dynamic masking is applied, user, such as a healthcare professional, may query database 212; secure tokenization module may automatically obscure patient names and other patient identifiers without the necessary clearance, while allowing access to unmasked private data elements for authorized users such as attending physicians or medical researchers with specific access rights. Additionally, or alternatively, generating plurality of obfuscated data elements 224 may include shuffling, or rearranging values in a dataset or each private data element of plurality of private data elements 216 such that the values may be disconnected from plurality of private data elements 216. Further, secure tokenization module may be configured to add a pre-defined amount of random noise to plurality of private data elements 216 through noise addition or differential privacy as described in further detail below. As a non-limiting example, plurality of private data elements 216 may be altered while overall statistical properties of the database 212 may be maintained. Secure tokenization module may add a random value, for example, and without limitation, within a range of −2 or +2 years to each age entry within database 212. In this case, aggregate statistical analysis such as average age of the population, age distribution, and/or the like may remain accurate.

With continued reference to FIG. 2, in some cases, private data elements 216 may be encrypted using one or more cryptographic algorithms in order to generate one or more obfuscated data elements, wherein processor 204 may implement one or more cryptographic algorithms to render private data elements 216 unreadable without corresponding decryption key. In an embodiment, methods, and apparatus 200 described herein may perform or implement one or more aspects of a cryptographic system. A "cryptographic system," for the purpose of this disclosure, is a system that converts data from a first form, known as "plaintext," which is intelligible when viewed in its intended format, into a second form, known as "ciphertext," which is not intelligible when viewed in the same way. Ciphertext may be unintelligible in any format unless first converted back to plaintext. In one embodiment, a process of converting plaintext into ciphertext is known as "encryption." Encryption process may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

With continued reference to FIG. 2, in embodiments of cryptographic systems that are "asymmetric," either encryption or decryption key cannot be readily deduced without additional secret knowledge, even given the possession of a corresponding decryption or encryption key, respectively; an example is a "public key cryptographic system," in which possession of the encryption key does not make it practically feasible to deduce the decryption key, so that the encryption key may safely be made available to the public. An example of a public key cryptographic system is RSA, in which an encryption key involves the use of numbers that are products of very large prime numbers, but a decryption key involves the use of those very large prime numbers, such that deducing the decryption key from the encryption key requires the practically infeasible task of computing the prime factors of a number which is the product of two very large prime numbers. Another example is elliptic curve cryptography, which relies on the fact that given two points P and Q on an elliptic curve over a finite field, and a definition for addition where $A+B=-R$, the point where a line connecting point A and point B intersects the elliptic curve, where "0", the identity, is a point at infinity in a projective plane containing the elliptic curve, finding a number k such that adding P to itself k times results in Q is computationally impractical, given correctly selected elliptic curve, finite field, and P and Q.

With continued reference to FIG. 2, in some cases, at least an obfuscated data element within set of obfuscated data elements 224 may include a cryptographic hash. In some embodiments, apparatus 200, and methods described herein may produce one or more cryptographic hashes, also referred to by the equivalent shorthand term "hashes". A cryptographic hash, as used herein, is a mathematical representation of a lot of data, such as database 212 or plurality of private data elements 216 as described in further detail below; the mathematical representation is produced by a lossy "one-way" algorithm known as a "hashing algorithm." Hashing algorithm may be a repeatable process; that is, identical lots of data may produce identical hashes each time they are subjected to a particular hashing algorithm. Because hashing algorithm is a one-way function, it may be impossible to reconstruct a lot of data from a hash produced from the lot of data using the hashing algorithm. In the case of some hashing algorithms, reconstructing the full lot of data from the corresponding hash using a partial set of data from the full lot of data may be possible only by repeatedly guessing at the remaining data and repeating the hashing algorithm; it is thus computationally difficult if not infeasible for a single computer to produce the lot of data, as the statistical likelihood of correctly guessing the missing data may be extremely low. However, the statistical likelihood of a computer of a set of computers simultaneously attempting to guess the missing data within a useful timeframe may be higher, permitting mining protocols as described in further detail below.

With continued reference to FIG. 2, in an embodiment, hashing algorithm may demonstrate an "avalanche effect," whereby even extremely small changes to a data element may produce drastically different hashes. This may thwart attempts to avoid the computational work necessary to recreate a hash by simply inserting a fraudulent datum in data element, enabling the use of hashing algorithms for "tamper-proofing" data such as plurality of private data elements contained in database 212 as described above. This avalanche or "cascade" effect may be evinced by various hashing processes; persons skilled in the art, upon reading the entirety of this disclosure, will be aware of various suitable hashing algorithms for purposes described herein. Verification of a hash corresponding to plurality of private data elements 216 may be performed by running plurality of private data elements 216 through a hashing algorithm used to produce the hash. Such verification may be computationally expensive, albeit feasible, potentially adding up to significant processing delays where repeated hashing, or hashing of large quantities of data, is required, for instance as described in further detail below. Examples of hashing programs include, without limitation, SHA256, a NIST standard; further current and past hashing algorithms include Winternitz hashing algorithms, various generations of Secure Hash Algorithm (including "SHA-1," "SHA-2," and "SHA-3"), "Message Digest" family hashes such as "MD4," "MD5," "MD6," and "RIPEMD," Keccak, "BLAKE" hashes and progeny (e.g., "BLAKE2," "BLAKE-256," "BLAKE-512," and the like), Message Authentication Code ("MAC")-family hash functions such as PMAC, OMAC, VMAC, HMAC, and UMAC, Poly 1305-AES, Elliptic Curve Only Hash ("ECOH") and similar hash functions, Fast-Syndrome-based (FSB) hash functions, GOST hash functions, the Grøstl hash function, the HAS-160 hash function, the JH hash function, the RadioGatun hash function, the Skein hash function, the Streebog hash function, the SWIFFT hash function, the Tiger hash function, the Whirlpool hash function, or any hash function that satisfies, at the time of implementation, the requirements that a cryptographic hash be deterministic, infeasible to reverse-hash, infeasible to find collisions, and have the property that small changes to a private data element to be hashed will change the resulting hash so extensively that the original hash and the new hash appear uncorrelated to each other. A degree of security of a hash function in practice may depend both on the hash function itself and on characteristics of the private data element and/or digest used in the hash function. For example, where a data element is random, for a hash function that fulfills collision-resistance requirements, a brute-force or "birthday attack" may to detect collision may be on the order of $O(2^{n/2})$ for n output bits; thus, it may take on the order of $2^{256}$ operations to locate a collision in a 512 bit output "Dictionary" attacks on hashes likely to have been generated from a non-random original text can have a lower computational complexity, because the space of entries they are guessing is far smaller than the space containing all random permutations of bits. However, the space of possible data elements may be augmented by increasing the length or potential length of a possible data element, or by implementing a protocol whereby one or more randomly selected strings or sets of data are added to the data element, rendering a dictionary attack significantly less effective.

With continued reference to FIG. 2, generating set of obfuscated data elements 224 may include sampling from a noise distribution on a deidentified version of the plurality of private data elements 216. As used in this disclosure, a "noise distribution" is a mathematical model that defines how random variations i.e., "noise," are distributed or spread across a range of values. Processor 204 may sample from a noise distraction to introduce certain degreed of variability into plurality of private data elements 216 according to one or more properties of the chosen distribution, such as, without limitation, Gaussian (normal), uniform, Laplacian distributions, and/or the like. In some cases, noise distribution may determine an extent of randomness added to plurality of private data elements 216 within database 212. A "deidentified version" of private data element, for the purpose of this disclosure, is an (original) data element from which at least a part of the data element has been intentionally removed or altered to prevent identification of individuals. In one embodiment, deidentified version of a private data element may include a private data element from which PII (e.g., names, social security numbers, addresses, and other direct or indirect identifiers) of a corresponding individual has been removed to hinder subsequent re-identification.

With continued reference to FIG. 2, in one or more embodiments, processor 204 may be configured to apply a gaussian noise, uniform noise, Laplacian noise, and/or the like to one or more numerical or textural values in plurality of private data elements in a deidentified medical dataset to prevent an inference of specific patient information from biometric or health measurements. As a non-limiting example, database 212 may include a deidentified healthcare dataset containing information such as patient ages, diagnosis codes, treatment outcomes, among others but with all direct identifiers removed. Processor 204 may generate a set of obfuscated data elements 224 by sample from a gaussian noise distribution and add the sampled noise to private data elements describing the ages and treatment outcome values. For instance, and without limitation, if the original age of a patient is 45, adding gaussian noise with a mean of 0 and a standard deviation of 3 may alter the age to 48 in set of obfuscated data elements 224.

With continued reference to FIG. 2, processor 204 is configured to generate, using a generative model 228, set of obfuscated data elements 224 as a function of plurality of private data elements 216. A generative model may include a computational model designed to automatically generate obfuscated data elements as described herein. In an embodiment, generative model 228 may include a generative machine learning model as described in further detail below with reference to FIG. 4. In some cases, generative model 228 may implement one or more aspects of "generative artificial intelligence," a type of artificial intelligence (AI) that uses machine learning algorithms to create, establish, or otherwise generate data such as, without limitation, obfuscated data elements in various data modalities (e.g., text, image, video, audio, among others) that is similar to one or more provided training examples. In an embodiment, machine learning module described herein may generate one or more generative machine learning models that are trained on plurality of private data elements 216 within database 212. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

With continued reference to FIG. 2, processor 204 is configured to determine a first distance measure 232 between at least an obfuscated data element within set of obfuscated data elements 224 and at least a private data element of plurality of private data elements 216 within database 212. As used in this disclosure, a "distance measure" is a quantitative metric used to assess the degree of similarity or dissimilarity between two data elements or groups of data elements. In some cases, first distance measure 232 may possess one or more properties of a metric space such as, without limitation, non-negativity, identity of indiscernible, symmetry, triangle inequality, and/or the like ensuring distance measure provide a consistent and reliable way to quantity similarity or difference. As a non-limiting example, distance measure may include a Euclidean distance i.e., a straight-line distance between two points in Euclidean space. As another non-limiting example, cosine similarity (i.e., measure of an angle between two vectors) may be used to measure a distance between at least an obfuscated data element within set of obfuscated data elements 224 and at least a private data element of plurality of private data elements 216. In one embodiment, cosine similarity may be computed as a function of using a dot product of the two vectors divided by the lengths of the two vectors, or the dot product of two normalized vectors. For instance, and without limitation, a cosine of 0° is 1, wherein it is less than 1 for any angle in the interval (0,π) radians. Cosine similarity may be a judgment of orientation and not magnitude, wherein two vectors with the same orientation have a cosine similarity of 1, two vectors oriented at 90° relative to each other have a similarity of 0, and two vectors diametrically opposed have a similarity of −1, independent of their magnitude. As a non-limiting example, vectors may be considered similar if parallel to one another. As a further non-limiting example, vectors may be considered dissimilar if orthogonal to one another. As a further non-limiting example, vectors may be considered uncorrelated if opposite to one another. Additionally, or alternatively, degree of similarity may include any other geometric measure of distance between vectors.

With continued reference to FIG. 2, as a non-limiting example, a distance measure between an obfuscated "age" attribute of 34 years and an original "age" attribute of 30 years may be 4 years (in this case, the distance measure may be an absolute difference). For obfuscation process, as described in further detail below, processor 204 may determine that any first distance measure of at least 3 years may be sufficient to obscure the original age. Other exemplary distance measure may include, without limitation, hamming distance, Jaccard index, and/or the like. As persons skilled in the art, upon reviewing the entirety of this disclosure, will be aware of various distance measure may be employed to ensure that the generated obfuscated data element is substantially different from the private data element. It should be noted that, the choice of first distance measure 232 and threshold for sufficient obfuscation as described herein may vary, depending on the nature of data elements, privacy requirements of database 212, and/or the specific application or analysis for which the obfuscated data elements are intended.

With continued reference to FIG. 2, processor 204 may be configured to generate a set of finalized obfuscated data elements. As used in this disclosure, a "finalized obfuscated data element" is an end product of data obfuscation as described herein where a plurality of private data elements have undergone one or more transformations to conceal or alter the value of the data elements subsequent to refinement, evaluation, and/or adjustment, satisfying pre-defined privacy, security, or utility criteria. In one embodiment, set of finalized obfuscated data elements may be analytically-ready, operationally-ready, and/or research-ready. In some cases, set of finalized obfuscated data elements may comply with data protection regulations and standards such as, without limitation, GDPR, HIPAA, or CCPA which mandate the protection of personal and sensitive data. As a non-limiting example, set of finalized obfuscated data elements may be irreversible without specific keys or additional information. Plurality of private data elements 216 may not be reconstructed from set of finalized obfuscated data elements without substantial effort. Set of finalized obfuscated data elements may include any obfuscated data elements within set of obfuscated data elements 224 as described above with, or without any adjustments and/or modifications.

With continued reference to FIG. 2, processor 204 is configured to verify, for at least an obfuscated data element within set of obfuscated data elements 224, first distance measure 232 is within a distance range 236. Processor 204 may be configured to select a subset of obfuscated data elements 240 from set of obfuscated data elements 224 as a function of the verification and transmit the selected subset of obfuscated data elements to one or more requesting entities within a computing environment as described in further detail below. As used in this disclosure, a "distance range" is a specified range of values that sets boundaries of distance measures, for example within which an obfuscated data element deviate from private data element (i.e., the degree of alteration or obfuscation of data element from its original form) is considered acceptable. In some cases, distance range 236 as described herein may be based on one or more pre-defined requirements or criteria for obfuscation and user's need to balance privacy protection with the utility of the obfuscated data elements.

With continued reference to FIG. 2, distance range 236 includes a minimum threshold and a maximum threshold. As a non-limiting example, verifying first distance measure 232 against distance range 236 may include verifying first distance measure 232 is greater than minimum threshold e.g., a minimum distance $D_{min}$, and is less than a maximum threshold e.g., a maximum distance $D_{max}$, from at least a pre-determined number M of private data elements of plurality of private data elements 216. In one embodiment, $D_{min}$ may ensure obfuscated data elements are substantially different from private data elements while $D_{max}$ may ensure obfuscated data elements do not deviate too much from private data elements thereby preserving the utility for further processing steps as described below. In some cases, user may manually determine M, the parameter that specify a desired number of private data elements that should fall within distance range 236 as described herein; for instance, and without limitation, user may input a minimum number of private data elements that should fall within $D_{max}$ threshold to an obfuscated data element to set a desired level of similarity across database 212 for analytical consistency. Processor 204 may be configured to evaluate, at least an obfuscated data element within set of obfuscated data elements 224 to check, based on corresponding first distance measure, its modified state falls within distance range 236 from its original state indicated by the corresponding private data element.

With continued reference to FIG. 2, in one or more embodiments, verifying first distance measure 232 is within distance range 236 may include assessing a similarity or dissimilarity of at least an obfuscated data element is within distance range i.e., $D_{min}$ to $D_{max}$. In such embodiments, processor 204 may verify at least an obfuscated data element within set of obfuscated data elements 224 is neither too similar (e.g., risking privacy) nor too dissimilar (e.g., risking utility) from at least a private data element of plurality of private data elements 216 within database 212. Processor 204 may select one or more obfuscated data elements i.e., "subset of obfuscated data elements" that meet the above criteria set by distance range 236. Each obfuscated data elements within subset of obfuscated data elements 224 may have first distance measure falls within distance range 236. In some cases, selecting one or more obfuscated data elements may include, without limitation, aggregating similar obfuscated data elements (having smaller first distance measures), further noise addition, threshold/distance range adjustment (e.g., fine-tuning the thresholds based on one or more user feedbacks), data elements re-evaluation, synthetic data generation (for example, for data elements that still pose a risk of revealing sensitive information or do not meet the criteria), encryption, anonymity checks (e.g., k-anonymity, l-diversity, or t-closeness checks on sub set of obfuscated data elements 224), and/or the like.

With continued reference to FIG. 2, as a non-limiting example, database 212 may include plurality of private data elements 216 having complex data modalities such as images, audios, videos, or any other high-dimensional and detailed data types. In some cases, plurality of private data elements 216 may include one or more high-resolution medical images, such as, without limitation, X-rays, MRIs, or CT scans which contain detailed anatomical information that may be considered sensitive due to the potential for identifying the related patients from unique anatomical features or through image associated metadata. Generative model 228 as described above may include a conditional GAN (i.e., an extension of GAN model capable of receiving one or more additional conditioning inputs such as the deidentification parameter and obfuscation parameter as described in further detail below), trained on database 212 to generate, for example, without limitation, synthetic images, audios, videos, or the like that resemble plurality of private data elements 216 in terms of anatomical structures and pathological features relevant to patients and their medical diagnoses. For example, and as described above, generator may create new images while the discriminator may evaluate the created images against real images stored in database 212, refining generative model 228 until the synthetic data are indistinguishable from original ones to the untrained eye, yet do not correspond to any private data elements of plurality of private data elements 216 within database 212.

With continued reference to FIG. 2, verifying first distance measure 232 includes determining minimum threshold of distance range 236 as a function of a deidentification parameter 244 and determining maximum threshold of distance range 236 as a function of an obfuscation parameter 248. As used in this disclosure, a "deidentification parameter" is a quantitative or qualitative criterion used to guide the removing or modifying process of private data elements to prevent the identification of individuals. Such a private data element may include, in a non-limiting example, a personal identifier. In some cases, deidentification parameter 244 may include specific rule or thresholds for altering data, such as, without limitation, level of generalization, suppression noise addition required, privacy protection level, and/or the like. As a non-limiting example, deidentification parameter may specify all private data elements associated with direct identifiers (e.g., names, SSN, and the like) within plurality of private data elements 224 be removed and all private data elements associated with quasi-identifiers (e.g., zip codes, dates of birth, and the like) within plurality of private data elements 224 be aggregated or partially suppressed. An "obfuscation parameter," for the purpose of this disclosure, is a degree or manner in which private data elements are transformed or disguised to conceal its original state. In one embodiment, obfuscation parameter 248 may determine one or more maximum allowable changes to private data element to maintain the desired utility for its intended application subsequent to the obfuscation as described herein. In some cases, obfuscation parameter 248 may include a specification or an implementation of obfuscation algorithms to be applied (e.g., data masking, pseudonymization, synthetic data generation, and/or the like) and the extent to which these algorithms should alter plurality of private data elements 224.

With continued reference to FIG. 2, As a non-limiting example, minimum threshold $D_{min}$ (and potentially maximum threshold $D_{max}$) may be determined based on a privacy protection level (i.e., deidentification parameter 244) associated with at least one pre-determined domain. As used in this disclosure, a "privacy protection level" is a degree of confidentiality and security applied to prevent private data element or one or more parts of the private data element from unauthorized access or disclosure. In some cases, privacy protection level may be determined by assessing the sensitivity of private data elements, potential impact of private data elements exposure on individuals or entities, trusted regulatory or policy requirements, and/or the like. As a non-limiting example, privacy protection levels may be categorized into different tiers or classifications with each level indicating a strictness of privacy controls and measures that need to be implemented. A "pre-determined domain," for the purpose of this disclosure, is specific field, sector, or otherwise context for which original and/or obfuscated data elements are collected, stored, and/or processed as described herein. In some cases, each domain may have a distinct data types, privacy concerns, regulatory requirements, operational needs, and/or the like that affect how data elements are handled. Exemplary domains may include, without limitation, healthcare, finance, education, government, and/or the like.

With continued reference to FIG. 2, in some cases, a higher privacy protection level may necessitate a greater distance (e.g., greater minimum threshold $D_{min}$ and maximum threshold $D_{max}$ of distance range 236) between at least an obfuscated data element within set of obfuscated data elements 224 and at least a private data element of plurality of private data elements 216 within database 212 in order to reduce or minimize the risk of re-identification or data misuse. As a non-limiting example, in "healthcare" domain, privacy protection level may be determined based on the sensitivity of personal health information (PHI), wherein $D_{min}$ may be set higher than in, for example, "retail" domain due to the direct and indirect consequences of PHI exposure may be more significant (possibly leading to discrimination or personal distress), and wherein $D_{max}$ may be calibrated accordingly to ensure that sub set of obfuscated data elements 224 remain useful for clinical research or patient care analytics. As another non-limiting example, financial data elements may also require high privacy protection level to prevent fraud and protect user's financial integrity. Distance range 236, in this case, may be determined based privacy protection level defined by GDPR or CCPA. It should be noted, different domains may require different process to select and set the thresholds due to the varying implications of data exposure, sensitivity of data involved, specific regulatory requirements, and/or the like. As persons skilled in the art, upon reviewing the entirety of this disclosure, will be aware of different strategies of balancing privacy protection with the need for data utility to adapt the thresholds of the distance range.

With continued reference to FIG. 2, as another non-limiting example, maximum threshold $D_{max}$ and pre-determined number M of private data elements of plurality of private data elements may be determined based on an obfuscation risk tolerance level (i.e., obfuscation parameter 248). As used in this disclosure, an "obfuscation risk tolerance level" is a degree of risk an entity (e.g., organization) is willing to accept in relation to potential re-identification of users within subset of obfuscated data elements 224. In some cases, obfuscation risk tolerance level may vary across different domains listed above and entities. As a non-limiting example, obfuscation risk tolerance level may be categorized into "low," "medium," and "high," each indicating an aggressiveness of obfuscation process as described herein to be applied. In some cases, "healthcare" domain may exhibit a "low" obfuscation risk tolerance level due to the highly sensitive nature of PHI as described above and HIPAA requirements (e.g., breaches may have substantial negative consequences for patient privacy and organizational liability). Conversely, "education" domain may have a relatively lower obfuscation risk tolerance level. While student data privacy is important, the direct consequences of data breaches may be perceived as less severe than in "healthcare" or "finance" domain. As a non-limiting example, M may be automatically determined, by processor 204, based on a pre-determined obfuscation risk tolerance level. In some cases, a lower risk tolerance may result in a large M indicating a broader representation of database 212, while a higher risk tolerance level may allow for a smaller M indicating a narrower representation of database 212. For instance, and without limitation, one or more machine learning models as described herein may be used to predict or dynamically adjust, privacy protection level, obfuscation risk tolerance level, M, and any additional inputs necessitate in selecting subset of obfuscated data elements 240 as described herein.

With continued reference to FIG. 2, additionally, or alternatively, database 212 may include one or more patient audio records such as, without limitation, verbal descriptions of symptoms or patient-doctor consultations. In some cases, patient audio records may be received from a dialog agent as described in further detail below, wherein such patient audio records may include records of chat history between patients and medical professionals. In some cases, generating set of obfuscated data elements 224 may include applying voice conversion techniques to alter patient's voice in the audio records, replacing it with a synthetic voice, generated using generative model 228 that maintains the linguistic content but removes the identifiable voice characteristics and/or add relative context. As a non-limiting example, generative model 228 may implement one or more text-to-speech (TTS) systems coupled with a language processing module to convert private data elements, process textural information to remove or alter sensitive information, and utilize TTS to generate synthetic audio from the processed textural information.

With continued reference to FIG. 2, in one embodiment, language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 2, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

With continued reference to FIG. 2, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations. Alternatively, or additionally, language processing module may be produced using one or more large language models (LLMs) as described in further detail below.

With continued reference to FIG. 2, language processing module may use database 212 e.g., a corpus of documents to generate associations between language elements, and diagnostic engine may then use such associations to analyze words extracted from one or more documents and determine that the one or more documents indicate significance of a category. In an embodiment, language module and/or processor 204 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into processor 204. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

With continued reference to FIG. 2, in one or more embodiments, generative model 228 may include a combination of one or more (conditional) diffusion models for obfuscating data elements with various data modalities. As a non-limiting example, one or more diffusion models may be trained on database 212 containing one or more original images and generate new images by sampling from a noise distribution through a forward process (i.e., diffusion), wherein new images may be sufficiently distinct from training data as measured by first distance measure 232 and the constraint ($D_{min}$, $D_{max}$, M) as described above. In some cases, diffusion models may include a U-net based diffusion model having a model architecture primarily constructed from convolutional neural networks (convnets) as described in further detail below. In some cases, U-net based diffusion model may be characterized by a distinctive "U" shape which includes a plurality of convolution layers (containing up-convolutions), pooling layers, dropout layers, and/or the like. U-net based diffusion model is designed for efficient processing of image-type data elements, capturing both high-level and low-level (detailed) features within images. This is so, at least in part, because of U-net based diffusion model includes a symmetric expansive path which enable localization combined with a contracting path that captures the context of data elements. In some cases, a noisy image may be input into U-net base diffusion model, wherein the noisy image may be progressively refined to generate an output that is similar to the original data in structure and appearance but altered enough to ensure the deidentification adhering to the specified constraint ($D_{min}$, $D_{max}$, M).

With continued reference to FIG. 2, in some cases, one or more diffusion models may be pre-trained models; for instance, and without limitation, one or more diffusion models may include a transformer-based diffusion model. One or more diffusion models may, in some cases, implement a transformer architecture which use self-attention mechanisms as described in further detail below to process, for example, audiovisual data for one or more utilities as described herein that require understanding complex patterns and relationships between plurality of private data elements 216 in database 212. Such pre-trained models may be fine-turned based on distance range 236 to generate synthetic images, wherein the synthetic images, in some cases, may retain essential features of the original images within database 212. In other cases, processor 204 may fine-tune the generative model 228 by conditioning one or more diffusion models on a subset of private data elements selected from plurality of private data elements within database 212 corresponding to at least one target domain, wherein the subset of private data elements may include, without limitation, one or more text descriptions of the images. For example, and without limitation, specific image attributes or scenarios, such as generating training data for "healthcare" domain where accurately rendering health conditions are essential. It should be noted that, generative model 228 as described herein may be conditioned on various modalities (not just text but other data types such as environment sounds for audio or scene elements for images) without compromising on privacy or data protection standards.

With continued reference to FIG. 2, however, in practice, verifying outputs of generative model 228 e.g., set of obfuscated data elements 224 having first distance measures satisfy distance range may be challenging if database 212 size is large. Iteratively or recursively verifying, for at least an obfuscated data element within set of obfuscated data elements, first distance measure 232 is within the defined constraint $D_{min}$ (minimum distance/similarity from any private data element), $D_{max}$ (maximum distance/similarity to a set of private data elements), and M (the number of samples that should be at least as close as $D_{max}$) may be time consuming if database 212, for example, a training corpus contains substantial enough data to cause computational or storage challenges or that requires significant processing power for generative model 228 training and validation. As a non-limiting example, a large database may include hundreds of gigabytes of text data, reaching into terabytes for raw, unprocessed files, over millions images, or EHRs of millions of patients over multiple years. In one embodiment, apparatus 200, and method as described herein may address such challenge by clustering plurality of private data elements 216 within database 212 into a plurality of clusters using at least a clustering algorithm and selecting subset of obfuscated data elements 240 from set of obfuscated data elements 224 as a function of the plurality of clusters. In some cases, plurality of private data elements 216 and/or database 212 may be considered as one or more clusters.

With continued reference to FIG. 2, As a non-limiting example, at least a clustering algorithm may be implemented using a k-means clustering algorithm. A "k-means clustering algorithm" as used in this disclosure, includes cluster analysis that partitions n data elements into k clusters in which each private data element belongs to the cluster with the nearest mean. As used in this disclosure, a "cluster" is a group of data elements that are similar to each other based on certain criteria. "Cluster analysis," as used in this disclosure, includes grouping a set of data elements in way that data elements in the same group or cluster are more similar to each other than to those in other groups or clusters. In some cases, clustering plurality of private data elements 216 within database 212 into plurality of clusters may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. In some cases, cluster analysis may include hard clustering whereby each data element belongs to a cluster or not. In some cases, cluster analysis may include soft clustering or fuzzy clustering whereby each data element belongs to each cluster to a certain degree such as for example a likelihood of belonging to a cluster; for instance, and without limitation, a fuzzy clustering algorithm may be used to identify clustering of private data elements of a first type or category with private data elements of a second type or category, and vice versa. In some cases, cluster analysis may include strict partitioning clustering whereby each data element belongs to exactly one cluster. In some cases, cluster analysis may include strict partitioning clustering with outliers whereby data elements may belong to no cluster and may be considered outliers. In some cases, cluster analysis may include overlapping clustering whereby data elements may belong to more than one cluster. In some cases, cluster analysis may include hierarchical clustering whereby data elements that belong to a child cluster also belong to a parent cluster.

With continued reference to FIG. 2, processor 204 may generate a k-means clustering algorithm receiving plurality of private data elements 216 from database 212 and outputs a definite number of classified data element clusters wherein the data element clusters each contain cluster data elements. In some cases, K-means algorithm may select a specific number of groups or clusters to output, identified by a variable "k." Generating a k-means clustering algorithm includes assigning inputs containing private data elements to a "k-group" or "k-cluster" based on feature similarity e.g., first distance measure 232. In one embodiment, each cluster of plurality of clusters may include a cluster centroid and a defined radius of influence. As used in this disclosure, a "cluster centroid" is a central data element having a mean position of all data elements in cluster. A "radius of influence," for the purpose of this disclosure, is a predefined distance around a cluster centroid within which data elements are considered to be part of that cluster. As a non-limiting example, radius of influence may essentially define a boundary or the extent to which the corresponding cluster's influence extends in multidimensional space where plurality of private data elements resides.

With continued reference to FIG. 2, in some cases, cluster centroid may be an average of all data elements in the cluster calculated separately for each dimension of the data points. In some cases, cluster centroid may include a representative of the cluster's location within the vector space in which plurality of private data elements 216 exists. Cluster centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance measure between cluster data element and cluster centroid. K-means clustering algorithm may calculate mean distance measure to a centroid as a function of k value, and the location of where the rate of decrease starts to sharply shift, this may be utilized to select a k value. Centroids of k-groups or k-cluster include a collection of feature values which are utilized to classify plurality of clusters containing private data elements. K-means clustering algorithm may act to identify clusters of closely related data elements, which may be provided with categorical data such as, without limitation, patient cohort labels; this may, for instance, generate an initial set of patient cohort labels from an initial set of data elements, and may also, upon subsequent iterations, identify new clusters to be provided new labels, to which additional data elements may be classified, or to which previously clustered private data elements may be reclassified.

With continued reference to FIG. 2, generating a k-means clustering algorithm may include generating initial estimates for cluster centroid or k centroids which may be randomly generated or randomly selected from plurality of private data elements. Cluster centroids may be utilized to define one or more clusters of plurality of clusters. K-means clustering algorithm may assign unclassified private data elements to one or more cluster centroids based on first distance measure, e.g., squared Euclidean distance, by first performing a data assigned step of unclassified data elements. In some cases, K-means clustering algorithm may assign unclassified private data element to its nearest cluster centroid based on the collection of centroids $c_i$ of centroids in set C. Unclassified private data element may be assigned to a cluster based on $\arg\min_{c_i \ni C} \text{dist}(c_i,x)^2$, where argmin includes argument of the minimum, $c_i$ includes a collection of cluster centroids in a set C, and dist includes standard Euclidean distance. In some cases, K-means clustering module may then recompute cluster centroids by taking mean of all cluster data elements assigned to centroid's cluster. This may be calculated based on $c_i = 1/|S_i| \Sigma x_i \ni S_i^{x_i}$. K-means clustering algorithm may continue to repeat these calculations until a stopping criterion has been satisfied such as when cluster data elements do not change clusters, the sum of the distances have been minimized, and/or some maximum number of iterations has been reached.

With continued reference to FIG. 2, clustering plurality of private data elements 216 may include determining a second distance measure and a third distance measure, for instance, and without limitation, k-means clustering algorithm may be configured to calculate degree of similarity index values between cluster centroid and a selected obfuscated data element (i.e., second distance measure). A "degree of similarity index value" as used in this disclosure, includes a distance measurement indicating a measurement between a cluster generated by at least a clustering algorithm and a selected data element. Degree of similarity index value may indicate how close a particular data element, or a combination of data elements is to being classified by k-means algorithm to a particular cluster. In some cases, K-means clustering algorithm may evaluate the distances of the combination of data elements to the k-number of clusters output by k-means clustering algorithm. As a non-limiting example, short distances between a data element and a cluster may indicate a higher degree of similarity between the data element and the cluster while longer distances between a data element and a cluster may indicate a lower degree of similarity between the data element and the cluster.

With continued reference to FIG. 2, in one embodiment, processor 204 may be configured to identify one or more clusters of plurality of clusters and identifying, as a function of second distance measure, one or more obfuscated data elements within set of obfuscated data elements 224 that fall within distance range 236. As a non-limiting example, the first identification process may determine which clusters are most representative or relevant, while the second identification process may ensure that selected obfuscated data elements are appropriately distanced from cluster centroids of plurality of clusters based on second distance measure. In such embodiment, processor 204 may no longer verify first distance measure of at least an obfuscated data element within set of obfuscated data elements 224 is within distance range 236, but instead, verify a distance measure between each cluster centroid of plurality of clusters (much less than the number plurality of private data elements 216 within database 212) and at least an obfuscated data element within set of obfuscated data elements 224 is within distance range 236, consistent with the constraint of ($D_{min}$, $D_{max}$, M) previously defined as described above.

With continued reference to FIG. 2, and continuing the non-limiting example, such direct verification with first distance measure may have a computational complexity of O(n×p) where n is the number of obfuscated data elements and p is the number of private data elements, assuming a distance measure calculation for each pair is O(1), and may become computationally intensive as either n or p grows. However, the cluster-based verification may have a computational complexity of O(n×k) where k is the number of clusters formed from plurality of private data elements 216 and where k<<n assuming the centroid of plurality of private data elements 216 is precomputed. Therefore, at least in part, cluster-based verification may be more scalable for larger database since it reduce the number of distance measure calculations by utilizing plurality of clusters. At least a clustering algorithm may reduce the problem space from comparing every obfuscated data element to every private data element to comparing at least an obfuscated data element to a significantly smaller number of cluster centroids. In some cases, private data elements that are outside the radius of influence of any cluster may be ignored and omitted during the said selection. It should be noted that, the above-described illustration of clustering plurality of private data elements 216 using k-means clustering is included for illustrative purposes only and should not be construed as limiting potential implementation of at least a clustering algorithm; persons skilled in the art, upon reviewing the entirety of this disclosure, will be aware of various additional or alternative clustering algorithms that may be used consistently with this disclosure.

With continued reference to FIG. 2, in some embodiments, subset of obfuscated data elements 240 may be displayed to a user. Display of information to a user is described above with reference to FIG. 1.

A system, method, apparatus or feature thereof may be consistent with any system, method, apparatus or feature thereof disclosed in U.S. patent application Ser. No. 18/643, 174, filed on Apr. 23, 2024, and titled "APPARATUS AND METHOD FOR GENERATING A MEDICAL DATABASE QUERY," U.S. patent application Ser. No. 18/662,750, filed on Mar. 29, 2024, and titled "SYSTEMS AND METHODS FOR RETRIEVING PATIENT INFORMATION USING LARGE LANGUAGE MODELS," and/or U.S. patent application Ser. No. 18/629,594, filed on Apr. 8, 2024, and titled "APPARATUS AND METHODS FOR GENERATING OBFUSCATED DATA WITHIN A COMPUTING ENVIRONMENT," the entirety of each of which is hereby incorporated by reference.

Figure 3C:
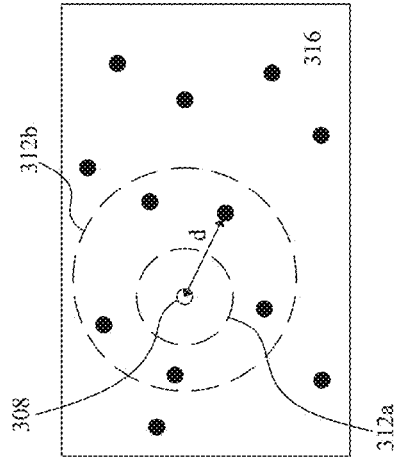
FIGS. 3A, 3B, and 3C are illustrations of exemplary scenarios of a distance measure verification process.
Figure 3B:
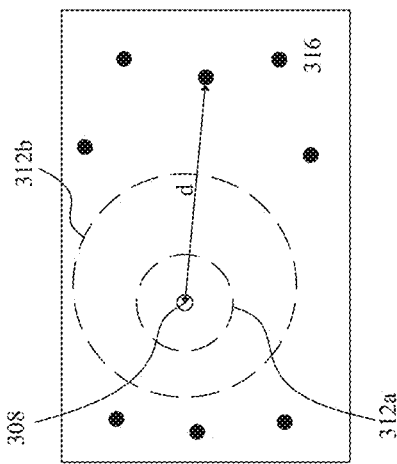
Figure 3A:
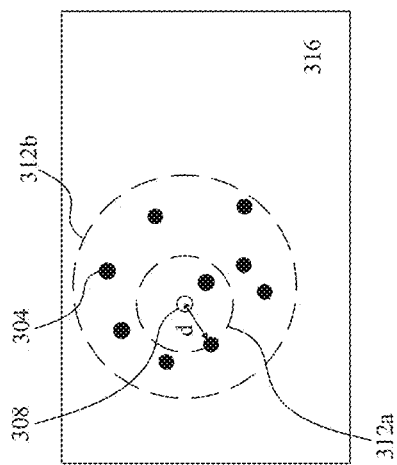

Now referring to FIGS. 3A-C, exemplary scenarios of a distance measure verification process are shown. In an embodiment, obfuscated data elements 304 (represented by black dots) may be positioned relative to at least a private data element 308 (represented by white dot) within a distance range indicated by a minimum threshold 312a (i.e., the innermost dashed circle) and a pre-determined maximum threshold 312b (i.e., the outermost dashed circle) in database 316 are illustrated. In some cases, at least a private data element 308 may include any one or plurality of private data elements within database 316. As a non-limiting example, at least a private data element 308 may include a cluster centroid of any cluster of plurality of clusters determined within database 316 as described above with reference to FIGS. 1 and 2.

In one embodiment, as shown in FIG. 3A, distance measure verification process may encounter a scenario where all generated obfuscated data elements 304 are too close to the centroid (i.e., at least a private data element 308). One or more obfuscated data elements 308 fall within minimum threshold 312a (i.e., $d \leq D_{min}$). In some cases, this may occur when the system's privacy protection is inadequate, for example, and without limitation, when privacy protection level as described above with reference to FIGS. 1 and/or 2 is low.

In another embodiment, as shown in FIG. 3B, distance measure verification process may encounter a scenario where all generated obfuscated data elements 308 fall too far from the centroid, lying outside maximum threshold (i.e., $d \geq D_{max}$). In some cases, this may occur when generated obfuscated data elements have lost substantial amount of original dataset's characteristics, potentially compromising the utility of the generated obfuscated data elements for analysis or modeling as described above with reference to FIGS. 1 and 2.

In a further embodiment, as shown in FIG. 3C, a scenario where generated obfuscated training data having an optimal distribution of data elements in relation to at least a private data element 308 defined by distance range may favor the distance measure verification process and further analysis or modeling such as, without limitation, training of one or more LLMs. In such an embodiment, data elements are neither too close nor too far from the centroid and exactly M=5 data elements lie within distance range (i.e., $D_{min} \leq d \leq D_{max}$), suggesting that obfuscated data elements may be sufficiently distanced from the centroid to be distinguishable from private data elements while still being representative (or related) enough for analytical utility as described above with reference to FIGS. 1 and 2.

Figure 4:
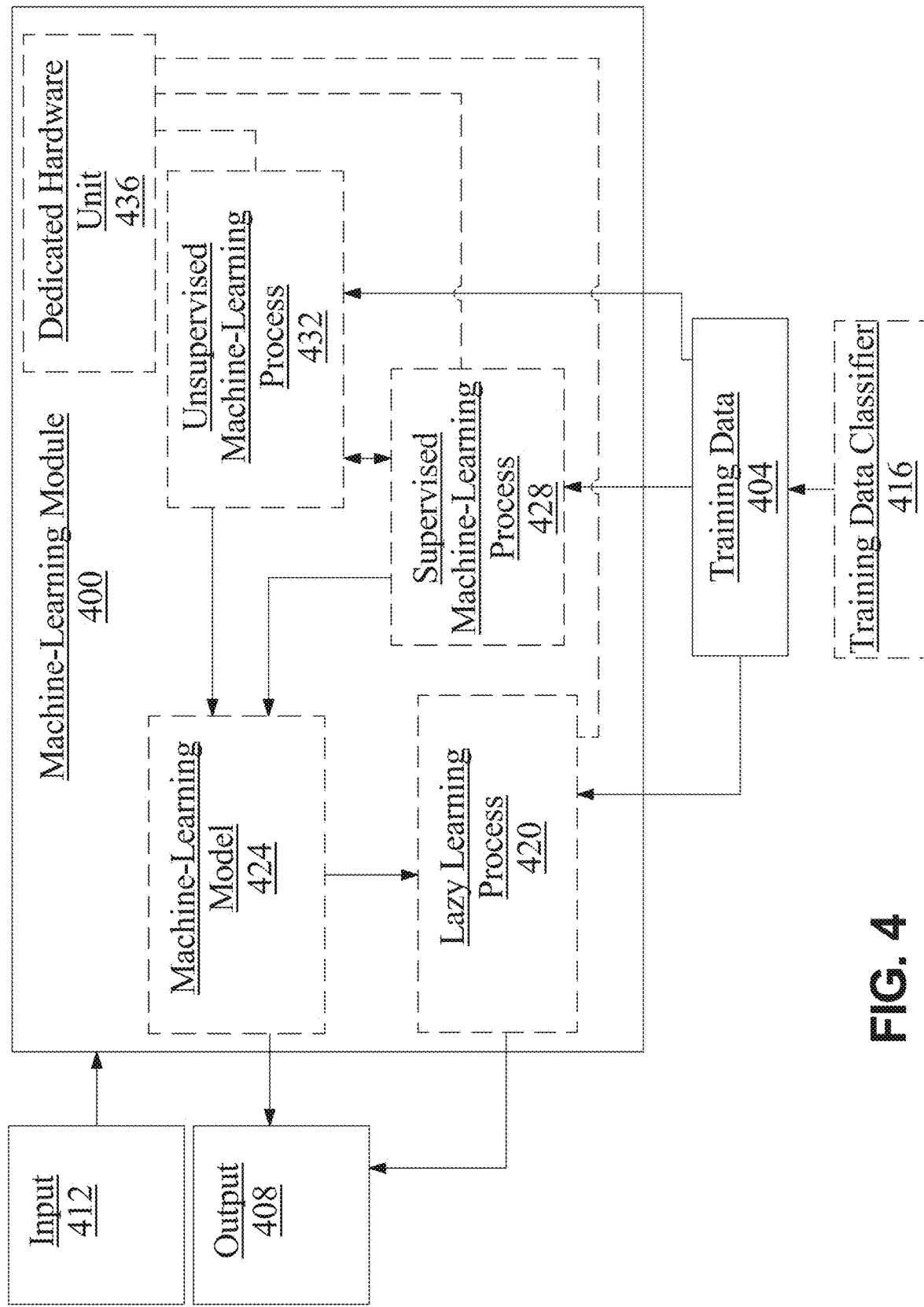
FIG. 4 is a box diagram of an exemplary machine learning model.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example, inputs may include audio data and outputs may include a text transcript of such audio data.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to particular words or languages.

Still referring to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of Scaling may be performed using a median value of a a set or subset of values:

$$X_{new} = \frac{X - X_{mean}}{\sigma}.$$

a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include audio data as described above as inputs, transcripts of audio data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 4, system 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 4, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; system 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 5:
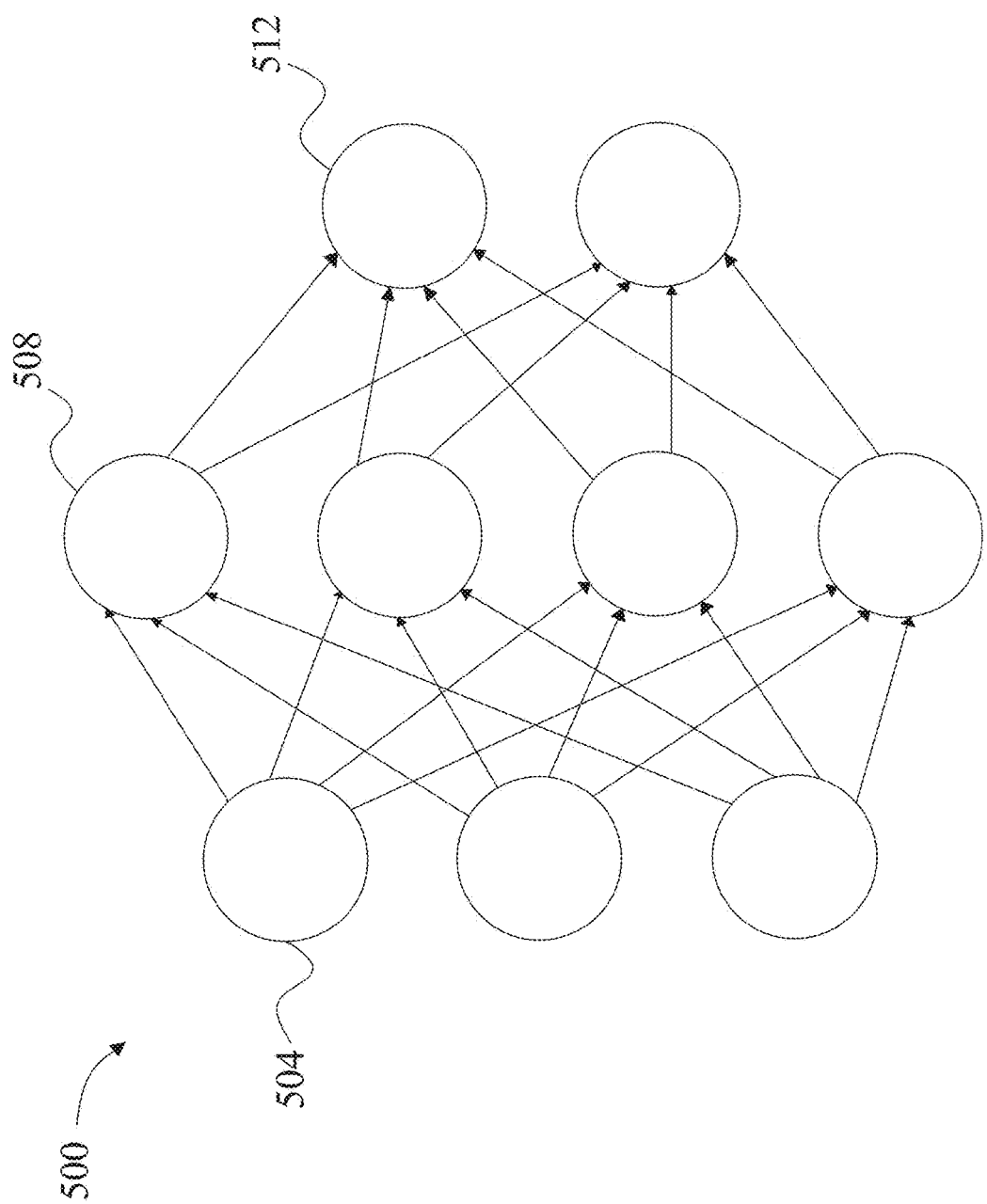
FIG. 5 is a diagram of an exemplary neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
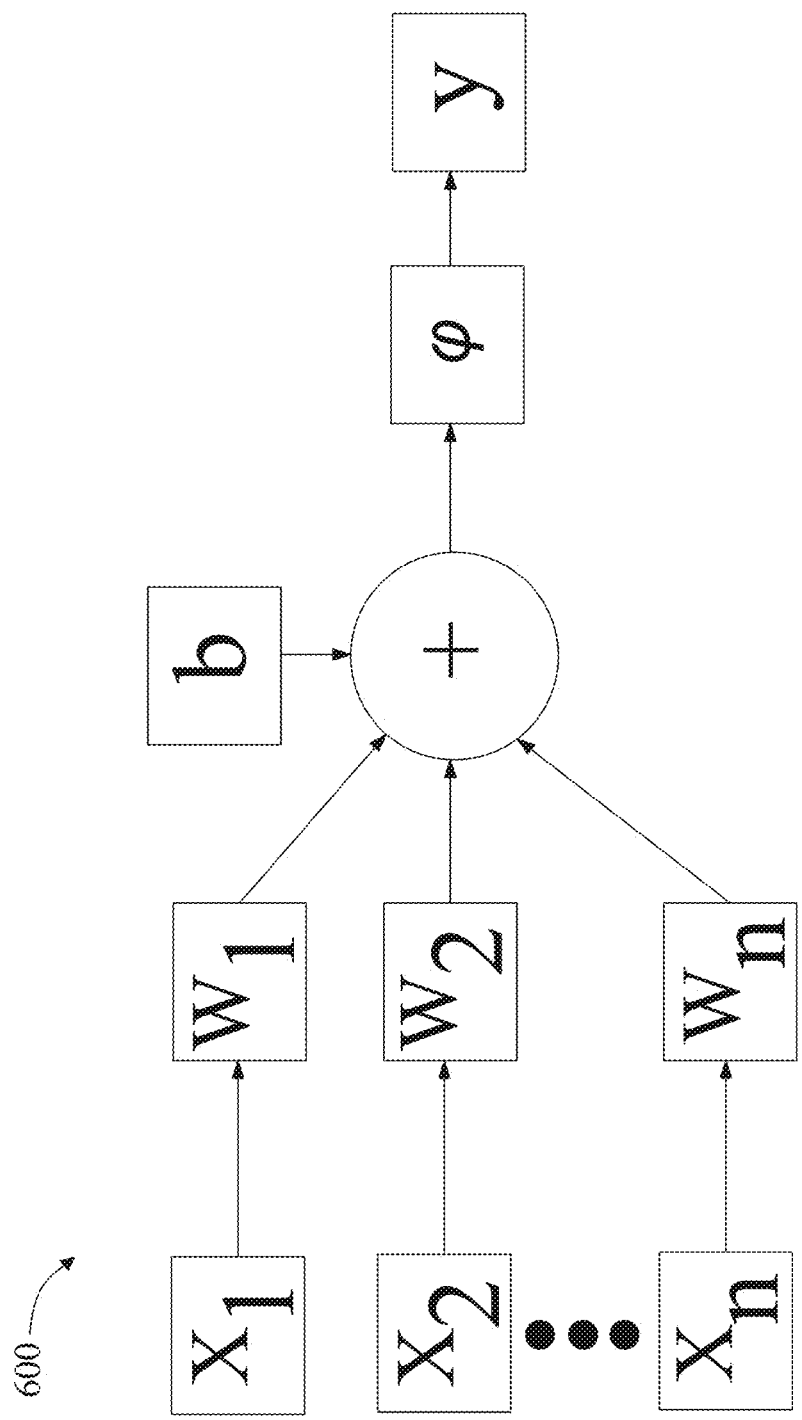
FIG. 6 is a diagram of an exemplary neural network node.

Referring now to FIG. 6, an exemplary embodiment of a node 600 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh derivative function, of the form $$\frac{e^x - e^{-x}}{e^x + e^{-x}},$$

a tanh (hyperbolic tangent) function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a\ (1+\tanh(\sqrt{2/\pi}(x+bx^r)))$ for some values of a, b, and r, and/or a scaled exponential linear unit function such as $$f(x) = \begin{cases} \alpha(e^x - 1) \text{ for } x < 0 \\ x \text{ for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 6, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Still referring to FIG. 6, in some embodiments, a convolutional neural network may learn from images. In non-limiting examples, a convolutional neural network may perform tasks such as classifying images, detecting objects depicted in an image, segmenting an image, and/or processing an image. In some embodiments, a convolutional neural network may operate such that each node in an input layer is only connected to a region of nodes in a hidden layer. In some embodiments, the regions in aggregate may create a feature map from an input layer to the hidden layer. In some embodiments, a convolutional neural network may include a layer in which the weights and biases for all nodes are the same. In some embodiments, this may allow a convolutional neural network to detect a feature, such as an edge, across different locations in an image.

Figure 7:
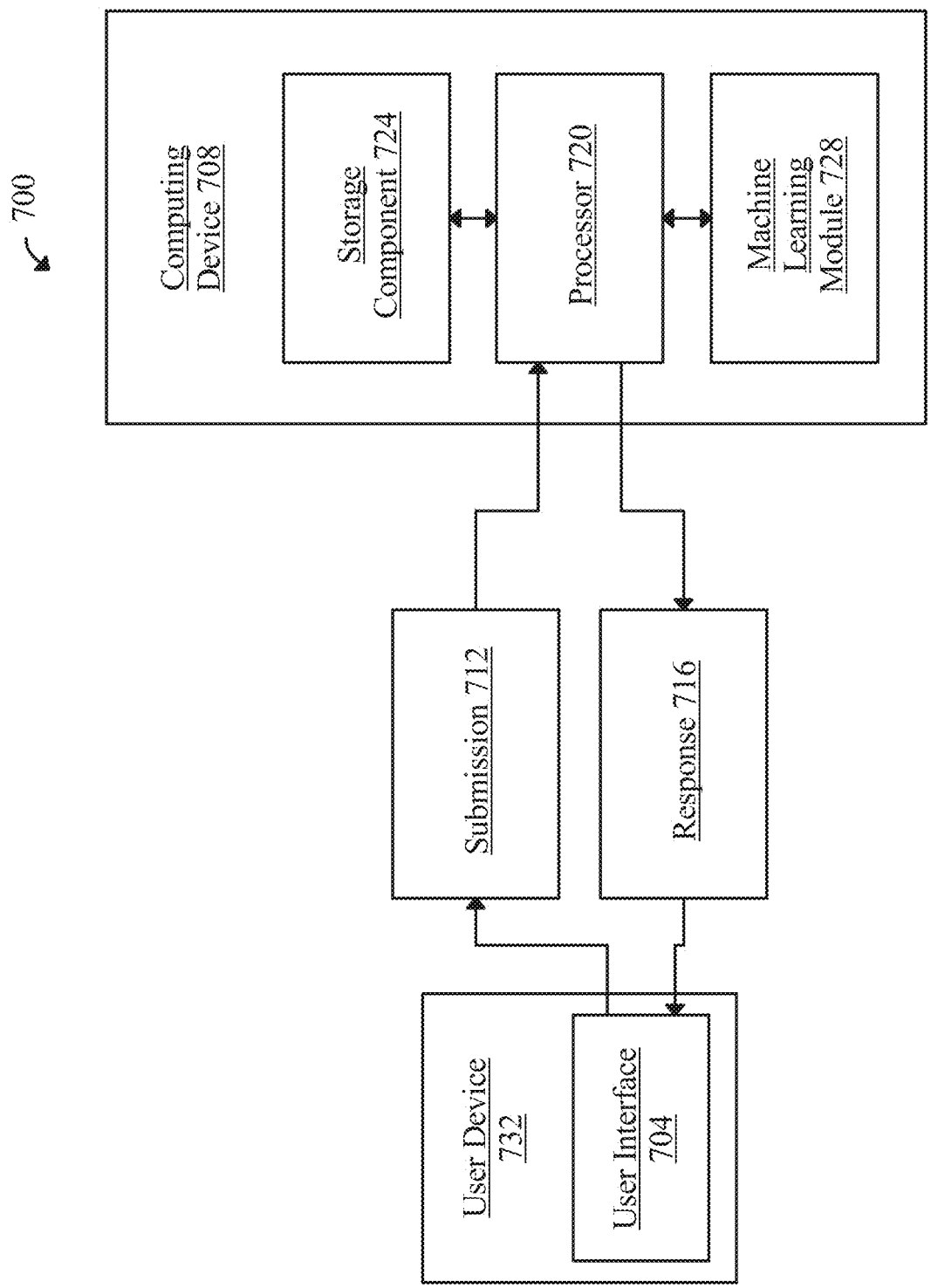
FIG. 7 is a box diagram of an exemplary system including a chatbot.

Now referring to FIG. 7, in some embodiments, apparatus 700 may communicate with user and/or instructor using a chatbot. According to some embodiments, user interface 704 on user device 732 may be communicative with a computing device 708 that is configured to operate a chatbot. In some embodiments, user interface 704 may be local to user device 732. In some embodiments, user interface 704 may be local to computing device 708. Alternatively, or additionally, in some cases, user interface 704 may remote to user device 732 and communicative with user device 732, by way of one or more networks, such as without limitation the internet. Alternatively, or additionally, one or more user interfaces may communicate with computing device 708 using telephonic devices and networks, such as without limitation fax machines, short message service (SMS), or multimedia message service (MMS). Commonly, user communicate with computing device 708 using text-based communication, for example without limitation using a character encoding protocol, such as American Standard for Information Interchange (ASCII). Typically, user interfaces conversationally interface with a chatbot, by way of at least a submission, from a user interface to the chatbot, and a response, from the chatbot to the user interface. For example, user interface 704 may interface with a chatbot using submission 712 and response 716. In some embodiments, submission 712 and/or response 716 may use text-based communication. In some embodiments, submission 712 and/or response 716 may use audio communication.

Still referring to FIG. 7, submission 712, once received by computing device 708 operating a chatbot, may be processed by a processor 720. In some embodiments, processor 720 processes submission 712 using one or more of keyword recognition, pattern matching, and natural language processing. In some embodiments, processor employs real-time learning with evolutionary algorithms. In some cases, processor 720 may retrieve a pre-prepared response from at least a storage component 724, based upon submission 712. Alternatively or additionally, in some embodiments, processor 720 communicates a response 716 without first receiving a submission, thereby initiating conversation. In some cases, processor 720 communicates an inquiry to user interface 704; and processor 720 is configured to process an answer to the inquiry in a following submission from the user interface. In some cases, an answer to an inquiry present within a submission from a user device may be used by computing device 708 as an input to another function. In some embodiments, computing device 708 may include machine learning module 728. Machine learning module 728 may include any machine learning models described herein. In some embodiments, submission 712 may be input into a trained machine learning model within machine learning module 728. In some embodiments, submission 712 may undergo one or more processing steps before being input into a machine learning model. In some embodiments, submission 712 may be used to train a machine learning model within machine learning module 728.

Figure 8:
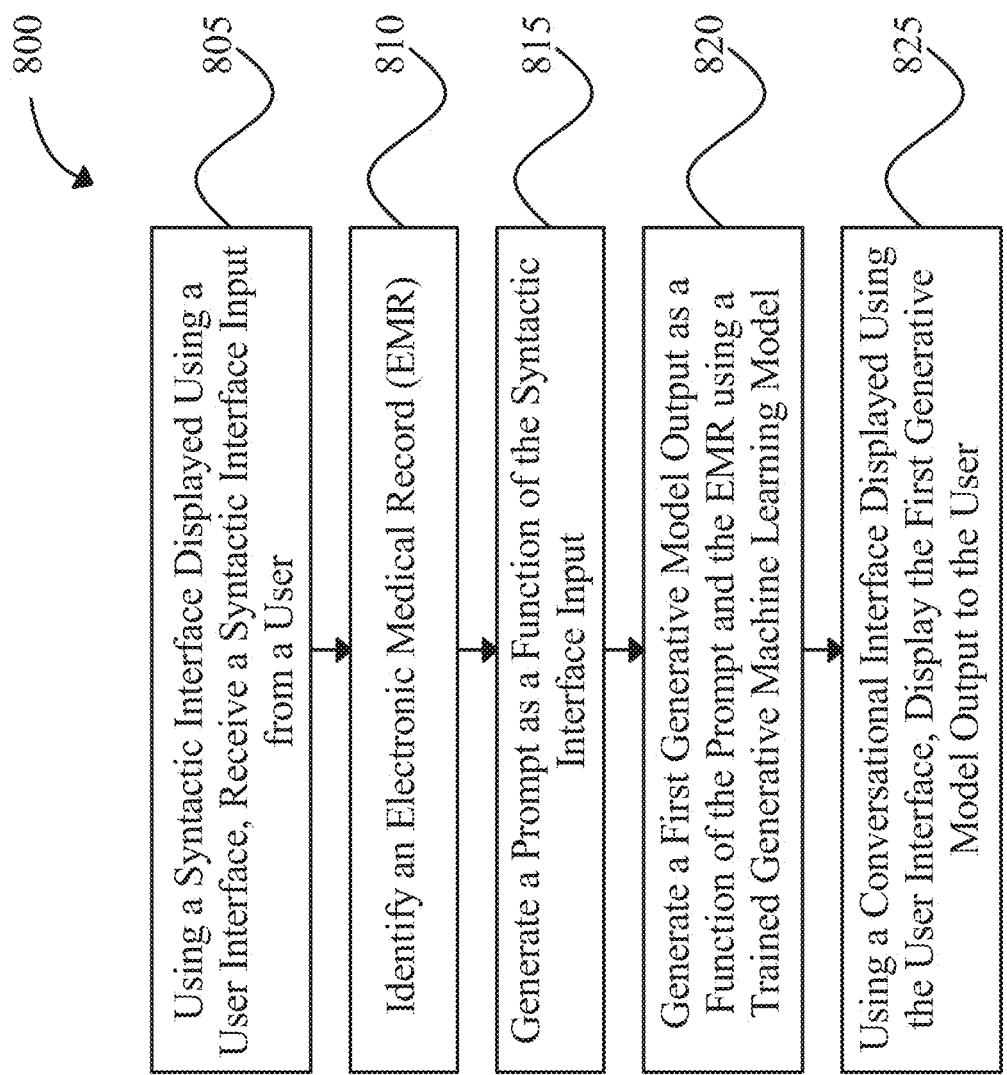
FIG. 8 is a flow diagram depicting an exemplary embodiment of a method of configuring a generative machine learning model using a syntactic interface.

Referring now to FIG. 8, an exemplary embodiment of a method 800 of configuring a generative machine learning model using a syntactic interface is illustrated. One or more steps if method 800 may be implemented, without limitation, as described with reference to other figures. One or more steps of method 800 may be implemented, without limitation, using at least a processor.

Still referring to FIG. 8, in some embodiments, method 800 may include a step 805 of using a syntactic interface displayed using a user interface, receiving a syntactic interface input from a user.

Still referring to FIG. 8, in some embodiments, method 800 may include a step 810 of identifying an electronic medical record (EMR). In some embodiments, an EMR may be identified by generating an EMR database query as a function of the syntactic interface input, querying an EMR database using the EMR database query, and receiving from the EMR database an EMR database response.

Still referring to FIG. 8, in some embodiments, method 800 may include a step 815 of generating a prompt as a function of the syntactic interface input. In some embodiments, the prompt is a natural language prompt. In some embodiments, the prompt is generated by inputting the first user input into a prompt template segment; and the EMR database query is generated by inputting the first user input into an EMR database query template segment.

Still referring to FIG. 8, in some embodiments, method 800 may include a step 820 of generating a first generative model output as a function of the prompt and the EMR using a trained generative machine learning model. In some embodiments, the generative machine learning model includes a large language model; and the first generative model output includes a natural language output.

Still referring to FIG. 8, in some embodiments, method 800 may include a step 825 of using a conversational interface displayed using the user interface, displaying the first generative model output to the user.

Still referring to FIG. 8, in some embodiments, method 800 may further include, using the at least a processor and the conversational interface, receiving a conversational interface input; using the at least a processor, generating a second generative model output as a function of the conversational interface input using the trained generative machine learning model; and using the at least a processor and the conversational interface, displaying the second generative model output to the user.

Still referring to FIG. 8, in some embodiments, method 800 may further include, using the at least a processor, training the generative machine learning model using an unsupervised learning algorithm. In some embodiments, the EMR database response includes a plurality of private data elements belonging to at least a private record; and generating a generative model output includes generating, using the generative machine learning model, a set of obfuscated data elements representative of the at least a private record, as a function of the plurality of private data elements. In some embodiments, method 800 may further include using the at least a processor, determining a first distance measure between at least an obfuscated data element within the set of obfuscated data elements and at least a private data element of the plurality of private data elements within the database; and using the at least a processor, verifying, for the at least an obfuscated data element within the set of obfuscated data elements, the first distance measure is within a distance range, wherein a minimum threshold of the distance range is determined as a function of a deidentification parameter; and a maximum threshold of the distance range is determined as a function of an obfuscation parameter. In some embodiments, method 800 may further include, using the at least a processor, fine-tuning the generative machine learning model on a subset of private data elements selected from the plurality of private data elements within the database corresponding to at least one pre-determined domain. In some embodiments, generating the set of obfuscated data elements includes sampling from a noise distribution on a deidentified version of the plurality of private data elements.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
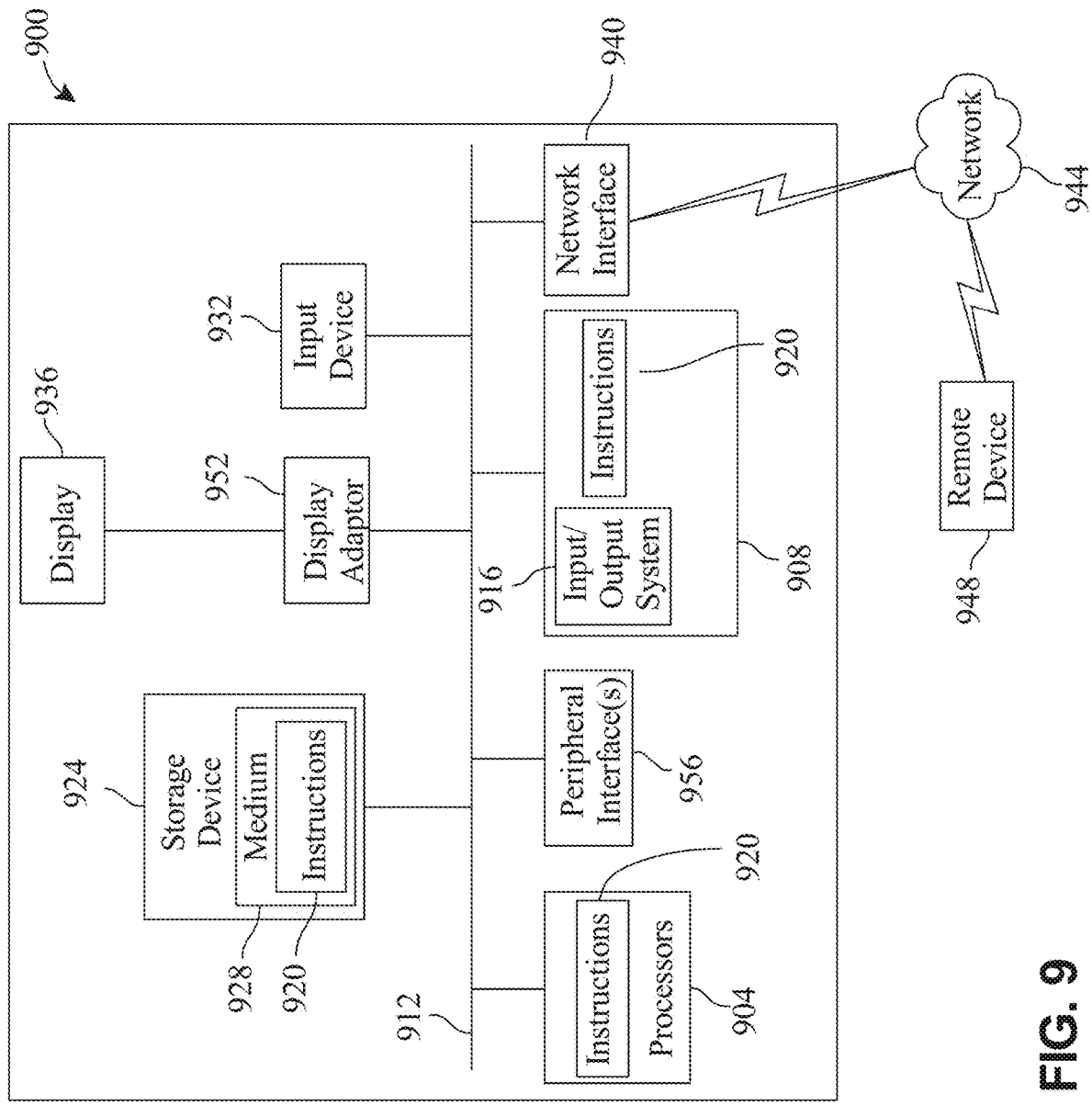
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display device 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for configuring a generative machine learning model using a syntactic interface, the system comprising:
   a user interface;
   at least a processor; and
   a memory communicatively connected to the at least processor, wherein the memory contains instructions configuring the at least processor to:
   using a syntactic interface displayed using the user interface, receive a syntactic interface input from a user;
   identify an electronic medical record (EMR) by:
      generating an EMR database query as a function of the syntactic interface input;
      querying an EMR database using the EMR database query; and
      receiving, from the EMR database, an EMR database response;
   generate a prompt as a function of the syntactic interface input;
   generate a first generative model output as a function of the prompt and the EMR using a trained generative machine learning model; and
   using a conversational interface displayed using the user interface, display the first generative model output to the user;
   wherein: the EMR database response comprises a plurality of private data elements belonging to at least a private record; and generating the generative model output comprises generating, using the generative machine learning model, a set of obfuscated data elements representative of the at least a private record, as a function of the plurality of private data elements;
      wherein the memory contains instructions configuring the at least processor to: determine a first distance measure between at least an obfuscated data element within the set of obfuscated data elements and at least a private data element of the plurality of private data elements within the database; and verify, for the at least an obfuscated data element within the set of obfuscated data elements, the first distance measure is within a distance range, wherein: a minimum threshold of the distance range is determined as a function of a deidentification parameter; and a maximum threshold of the distance range is determined as a function of an obfuscation parameter.

2. The system of claim 1, wherein:
the generative machine learning model comprises a large language model; and
the first generative model output comprises a natural language output.

3. The system of claim 1, wherein the memory contains instructions configuring the at least processor to:
using the conversational interface, receive a conversational interface input;
generate a second generative model output as a function of the conversational interface input using the trained generative machine learning model; and
using the conversational interface, display the second generative model output to the user.

4. The system of claim 1, wherein the prompt is a natural language prompt.

5. The system of claim 1, wherein:
wherein the memory contains instructions configuring the at least processor to generate the prompt by inputting the first user input into a prompt template segment; and
generating the EMR database query comprises inputting the first user input into an EMR database query template segment.

6. The system of claim 1, wherein the memory contains instructions configuring the at least processor to train the generative machine learning model using an unsupervised learning algorithm.

7. The system of claim 1, wherein the memory contains instructions configuring the at least processor to fine-tune the generative machine learning model on a subset of private data elements selected from the plurality of private data elements within the database corresponding to at least one pre-determined domain.

8. The system of claim 1, wherein generating the set of obfuscated data elements comprises sampling from a noise distribution on a deidentified version of the plurality of private data elements.

9. A method of configuring a generative machine learning model using a syntactic interface, the method comprising:
using at least a processor and a syntactic interface displayed using a user interface, receiving a syntactic interface input from a user;
using the at least a processor, identifying an electronic medical record (EMR) by:
generating an EMR database query as a function of the syntactic interface input;
querying an EMR database using the EMR database query; and
receiving, from the EMR database, an EMR database response;
using the at least a processor, generating a prompt as a function of the syntactic interface input;
using the at least a processor, generating a first generative model output as a function of the prompt and the EMR using a trained generative machine learning model; and
using the at least a processor and a conversational interface displayed using the user interface, displaying the first generative model output to the user;
wherein: the EMR database response comprises a plurality of private data elements belonging to at least a private record; and generating the generative model output comprises generating, using the generative machine learning model, a set of obfuscated data elements representative of the at least a private record, as a function of the plurality of private data elements;
wherein the method further comprises: using the at least a processor, determining a first distance measure between at least an obfuscated data element within the set of obfuscated data elements and at least a private data element of the plurality of private data elements within the database; and using the at least a processor, verifying, for the at least an obfuscated data element within the set of obfuscated data elements, the first distance measure is within a distance range, wherein: a minimum threshold of the distance range is determined as a function of a deidentification parameter; and a maximum threshold of the distance range is determined as a function of an obfuscation parameter.

10. The method of claim 9, wherein:
the generative machine learning model comprises a large language model; and
the first generative model output comprises a natural language output.

11. The method of claim 9, wherein the method further comprises:
using the at least a processor and the conversational interface, receiving a conversational interface input;
using the at least a processor, generating a second generative model output as a function of the conversational interface input using the trained generative machine learning model; and
using the at least a processor and the conversational interface, displaying the second generative model output to the user.

12. The method of claim 9, wherein the prompt is a natural language prompt.

13. The method of claim 9, wherein:
the prompt is generated by inputting the first user input into a prompt template segment; and
the EMR database query is generated by inputting the first user input into an EMR database query template segment.

14. The method of claim 9, wherein the method further comprises, using the at least a processor, training the generative machine learning model using an unsupervised learning algorithm.

15. The method of claim 9, wherein the method further comprises, using the at least a processor, fine-tuning the generative machine learning model on a subset of private data elements selected from the plurality of private data elements within the database corresponding to at least one pre-determined domain.

16. The method of claim 9, wherein generating the set of obfuscated data elements comprises sampling from a noise distribution on a deidentified version of the plurality of private data elements.

\* \* \* \* \*